(12) United States Patent
Duncan

(10) Patent No.: US 11,325,943 B2
(45) Date of Patent: May 10, 2022

(54) CRYSTALLINE SALT FORMS OF SBT-20

(71) Applicant: Stealth BioTherapeutics Corp., Grand Cayman (KY)

(72) Inventor: Scott M. Duncan, Bedford, MA (US)

(73) Assignee: STEALTH BIOTHERAPEUTICS INC., Needham, MA (US)

( * ) Notice: Subject to any disclaimer, the term of this patent is extended or adjusted under 35 U.S.C. 154(b) by 0 days.

(21) Appl. No.: 16/492,521

(22) PCT Filed: Jun. 1, 2018

(86) PCT No.: PCT/US2018/035658
§ 371 (c)(1),
(2) Date: Sep. 9, 2019

(87) PCT Pub. No.: WO2018/223032
PCT Pub. Date: Dec. 6, 2018

(65) Prior Publication Data
US 2021/0292361 A1 Sep. 23, 2021

Related U.S. Application Data

(60) Provisional application No. 62/514,051, filed on Jun. 2, 2017.

(51) Int. Cl.
*A61K 38/00* (2006.01)
*A61P 27/02* (2006.01)
*C07K 5/09* (2006.01)
*C07K 5/107* (2006.01)

(52) U.S. Cl.
CPC ............ *C07K 5/1016* (2013.01); *A61K 38/00* (2013.01)

(58) Field of Classification Search
CPC ....... A61K 38/00; A61P 27/02; C07K 5/0817; C07K 5/1019; C07K 5/09
See application file for complete search history.

(56) References Cited

U.S. PATENT DOCUMENTS

| | | | |
|---|---|---|---|
| 8,697,657 B2 * | 4/2014 | Wilson | A61P 9/10 514/21.9 |
| 2014/0093897 A1 * | 4/2014 | Szeto | A61P 43/00 435/21 |
| 2016/0151446 A1 * | 6/2016 | Wilson | A61K 38/07 514/1.9 |

FOREIGN PATENT DOCUMENTS

| WO | WO-2015183984 A2 * | 12/2015 | ........... C07K 5/1016 |
|---|---|---|---|
| WO | WO-2017/120470 A1 | 7/2017 | |
| WO | WO-2018/223032 A1 | 12/2018 | |

OTHER PUBLICATIONS

Dai et al., "Cardioprotective Effects of Mitochondria-Targeted Peptide SBT-20 in two Different Models of Rat Ischemia/Reperfusion," Cardiovascular Drugs and Therapy, 30(6): 559-566 (2016).
International Search Report and Written Opinion for International Application No. PCT/US2018/035658 dated Aug. 13, 2018.

* cited by examiner

*Primary Examiner* — Julie Ha
(74) *Attorney, Agent, or Firm* — Dana M. Gordon; Foley Hoag LLP

(57) ABSTRACT

Disclosed are various crystalline salt forms of L-Phe-D-Arg-L-Phe-L-Lys-$NH_2$.

14 Claims, 7 Drawing Sheets

CRYSTALLINE SALT FORMS OF SBT-20

RELATED APPLICATION

This application is the 35 U.S.C. 371 national phase of International Patent Application No. PCT/US2018/35658, filed Jun. 1, 2018, which claims benefit of priority to U.S. Provisional Patent Application No. 62/514,051, filed Jun. 2, 2017.

BACKGROUND

Through oxidative phosphorylation, mitochondria convert nutrients and oxygen into adenosine triphosphate (ATP), the chemical transporter of energy in most aerobic organisms. The electron transport chain (ETC) of mitochondria represents the primary source of ATP, as well as a source of reactive oxygen species (ROS). Mitochondrial dysfunction results in less ATP production and, as a result, insufficient energy to maintain the cell. Such dysfunction also results in excessive ROS production, spiraling cellular injury, and ultimately apoptosis of the cell. Mitochondrial dysfunction, is a key element believed to be at the root of a variety of serious, debilitating diseases.

Natural antioxidants, such as coenzyme Q and vitamin E, have been shown to provide some protection of the cell from damage induced by elevated ROS levels associated with mitochondrial dysfunction. However, antioxidants or oxygen scavengers have also been shown to reduce ROS to unhealthy levels and may not reach the ETC in sufficient concentrations to correct the mitochondrial imbalance. Therefore, there is a need for novel compounds that can selectively target the ETC, restore efficient oxidative phosphorylation, and, thereby, address mitochondrial disease and dysfunction.

DETAILED DESCRIPTION

The present invention features salts of Compound (I)

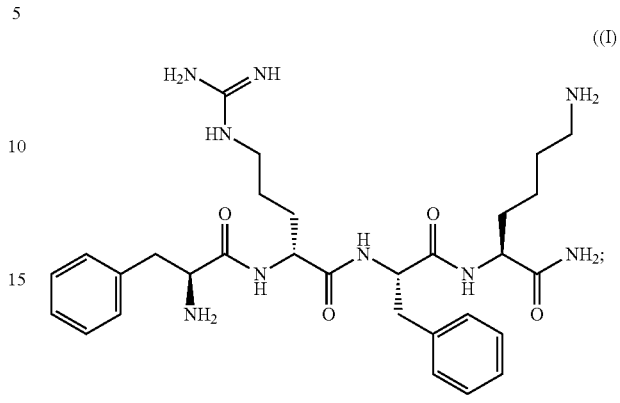

(I)

SBT-020; L-Phe-D-Arg-L-Phe-L-Lys-$NH_2$). Compound (I) has been shown to affect the mitochondrial disease process by helping to protect organs from oxidative damage caused by excess ROS production and to restore normal ATP production.

A crystalline form of a salt of Compound (I) can be used to modulate/improve the physicochemical properties of the compound, including but not limited to solid state properties (e.g., crystallinity, hygroscopicity, melting point, or hydration), pharmaceutical properties (e.g., solubility/dissolution rate, stability, or compatibility), as well as crystallization characteristics (e.g., purity, yield, or morphology).

In certain embodiments, the present invention provides a pharmaceutical preparation comprising a crystalline salt of Compound (I) and one or more pharmaceutically acceptable excipients. In certain embodiments, the pharmaceutical preparations may be for use in treating or preventing a condition or disease as described herein.

In certain embodiments, a polymorph of the crystalline salt is characterized by powder X-ray diffraction (XRD). θ represents the diffraction angle, measured in degrees. In certain embodiments, the diffractometer used in XRD measures the diffraction angle as two times the diffraction angle θ. Thus, in certain embodiments, the diffraction patterns described herein refer to X-ray intensity measured against angle 2θ.

In certain embodiments, a crystalline salt of Compound (I) is not solvated (e.g., the crystal lattice does not comprise molecules of a solvent). In certain alternative embodiments, a crystalline salt of Compound (I) is solvated. In some cases, the solvent is water.

In one aspect, the invention features a crystalline form of Compound (I) which has characteristic peaks in the powder X-ray diffraction (XRPD) pattern as shown in any one of FIGS. 1-5.

In another aspect, the invention features a crystalline form of Compound (I) which has characteristic peaks in the powder X-ray diffraction (XRPD) pattern at values of two theta (° 2θ) as shown in any one of Tables 32-36.

The relative intensity, as well as the two theta value, of each peak in Tables 32-36, as well as in FIGS. 1-5, may change or shift under certain conditions, although the crystalline form is the same. One of ordinary skill in the art should be able to determine readily whether a given crystalline form is the same crystalline form as described in one of Tables 32-36, as well as in FIGS. 1-5, by comparing their XRPD data.

Figure 1:
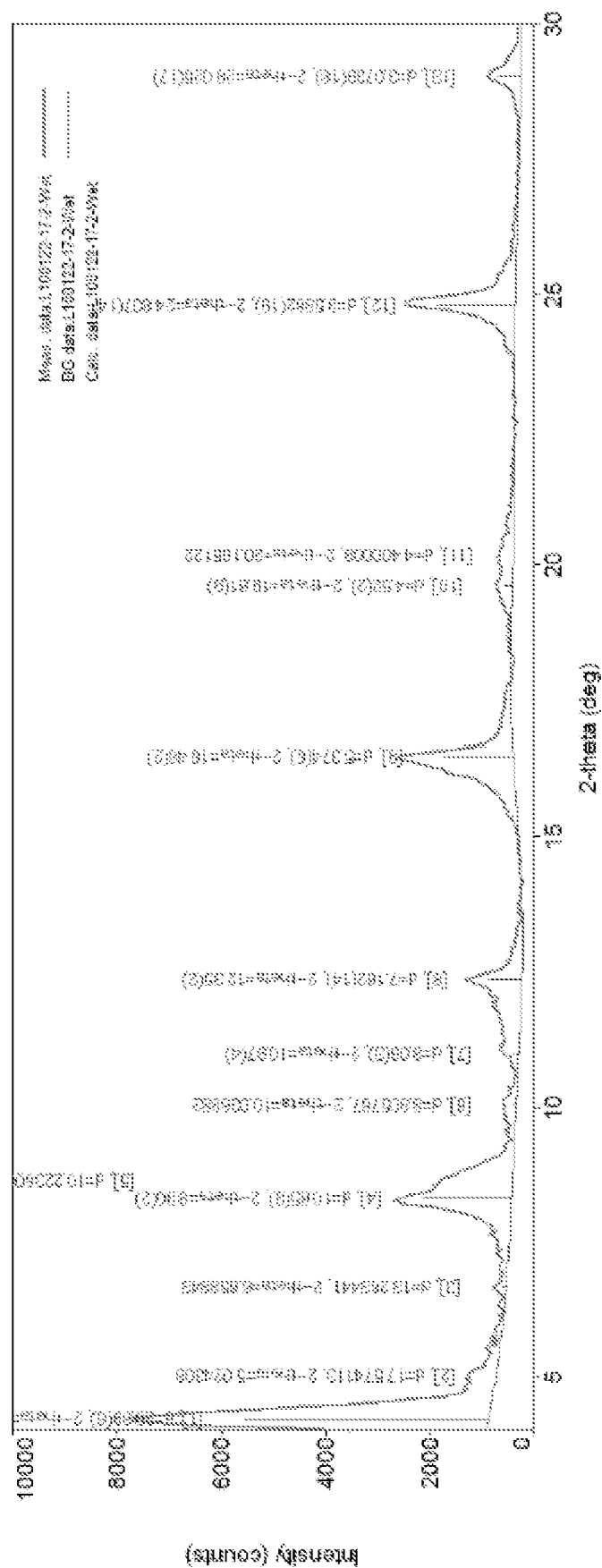
FIG. 1 depicts an XRPD pattern 1 of a L-lysine salt of Compound (I).

In yet another aspect, the invention features a crystalline form of a lysine salt of Compound (I) which has characteristic peaks in the powder X-ray diffraction (XRPD) pattern as shown in FIG. 1.

In yet another aspect, the invention features a crystalline form of a lysine salt of Compound (I) which has characteristic peaks in the powder X-ray diffraction (XRPD) pattern as shown in Table 32.

In another aspect, the invention features a crystalline form of a lysine salt of Compound (I) which has characteristic peaks in the powder X-ray diffraction (XRPD) pattern at values of two theta (° 2θ) of 4.2, 8.3, 12.3, 16.5, 24.8, and 29.0.

In another aspect, the invention features a crystalline form of a lysine salt of Compound (I) which has characteristic peaks in the powder X-ray diffraction (XRPD) pattern at values of two theta (° 2θ) of 4.2, 5.0, 6.6, 8.3, 8.6, 10.0, 11.0, 12.3, 16.5, 19.6, 20.2, 24.8, and 29.0.

Figure 2:
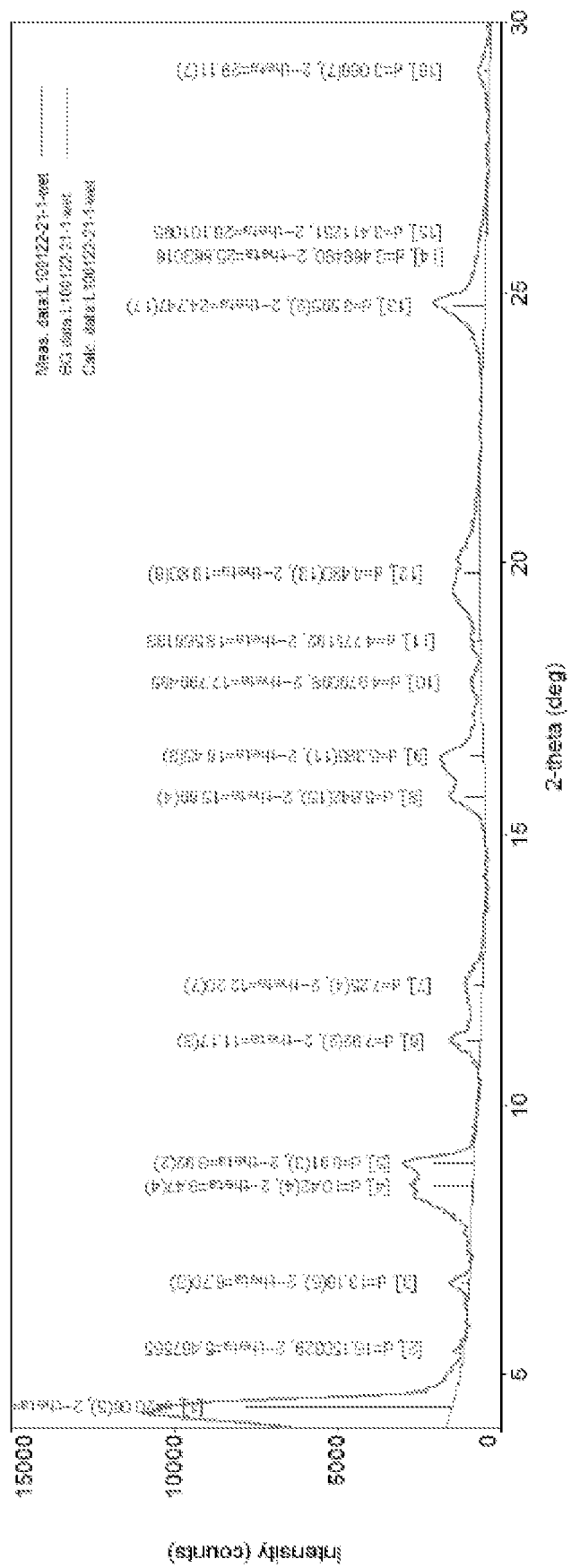
FIG. 2 depicts an XRPD pattern 2 of a L-lysine salt of Compound (I).

In yet another aspect, the invention features a crystalline form of a lysine salt of Compound (I) which has characteristic peaks in the powder X-ray diffraction (XRPD) pattern as shown in FIG. 2.

In yet another aspect, the invention features a crystalline form of a lysine salt of Compound (I) which has characteristic peaks in the powder X-ray diffraction (XRPD) pattern as shown in Table 33.

In another aspect, the invention features a crystalline form of a lysine salt of Compound (I) which has characteristic peaks in the powder X-ray diffraction (XRPD) pattern at values of two theta (° 2θ) of 4.4, 6.7, 8.5, 8.9, 11.2, 15.7, 16.4, 19.8, and 24.7.

In another aspect, the invention features a crystalline form of a lysine salt of Compound (I) which has characteristic peaks in the powder X-ray diffraction (XRPD) pattern at values of two theta (° 2θ) of 4.4, 5.5, 6.7, 8.5, 8.9, 11.2, 12.2, 15.7, 16.4, 17.8, 18.6, 19.8, 24.7, 25.7, 26.1, and 29.1.

Figure 3:
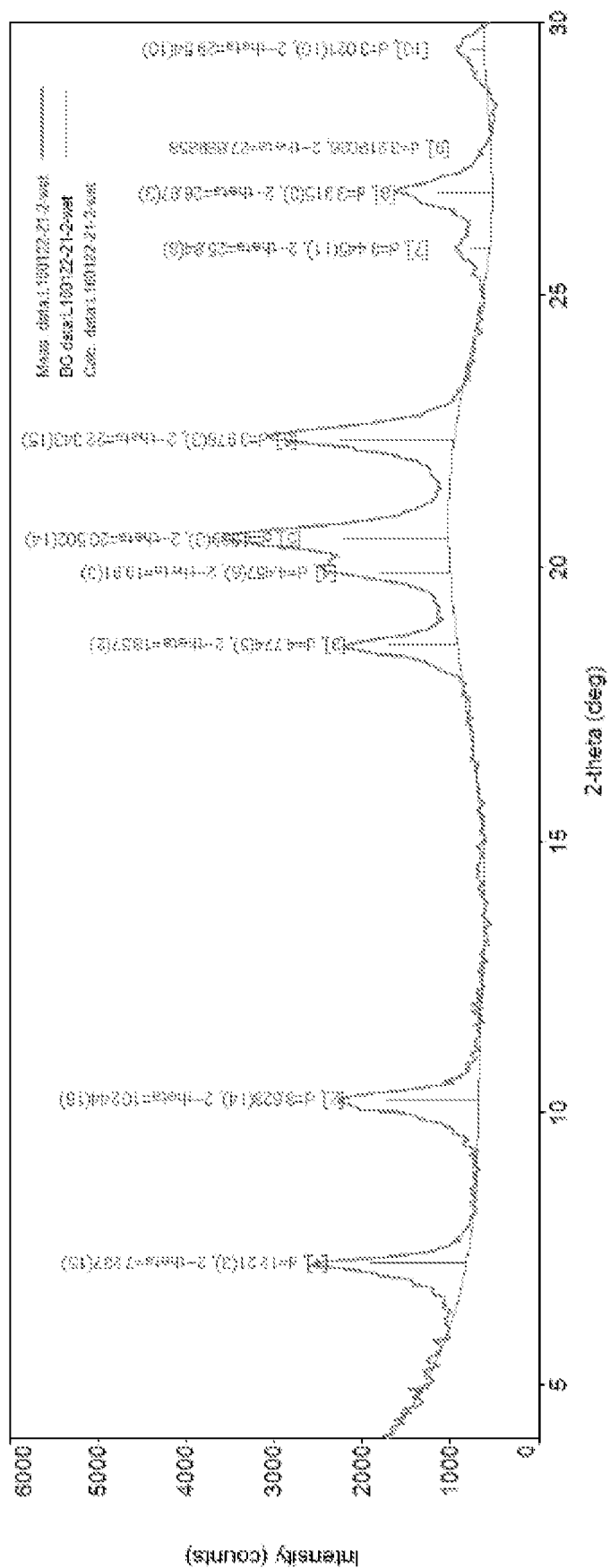
FIG. 3 depicts an XRPD pattern of a L-arginine salt of Compound (I).

In yet another aspect, the invention features a crystalline form of an arginine salt of Compound (I) which has characteristic peaks in the powder X-ray diffraction (XRPD) pattern as shown in FIG. 3.

In yet another aspect, the invention features a crystalline form of an arginine salt of Compound (I) which has characteristic peaks in the powder X-ray diffraction (XRPD) pattern as shown in Table 34.

In another aspect, the invention features a crystalline form of an arginine salt of Compound (I) which has characteristic peaks in the powder X-ray diffraction (XRPD) pattern at values of two theta (° 2θ) of 7.2, 10.2, 18.6, 19.9, 20.5, 22.3, and 26.9.

In another aspect, the invention features a crystalline form of an arginine salt of Compound (I) which has characteristic peaks in the powder X-ray diffraction (XRPD) pattern at values of two theta (° 2θ) of 7.2, 10.2, 18.6, 19.9, 20.5, 22.3, 25.8, 26.9, 27.7, and 29.5.

Figure 4:
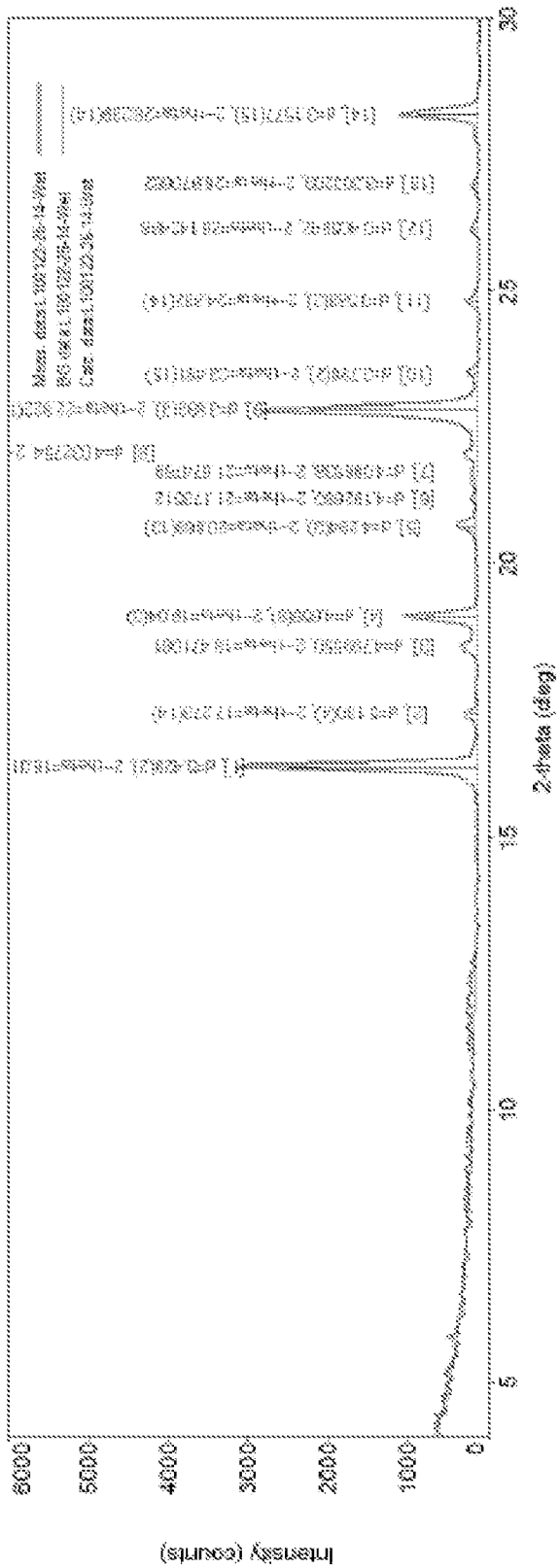
FIG. 4 depicts an XRPD pattern of a L-serine salt of Compound (I).

In yet another aspect, the invention features a crystalline form of a serine salt of Compound (I) which has characteristic peaks in the powder X-ray diffraction (XRPD) pattern as shown in FIG. 4.

In yet another aspect, the invention features a crystalline form of a serine salt of Compound (I) which has characteristic peaks in the powder X-ray diffraction (XRPD) pattern as shown in Table 35.

In another aspect, the invention features a crystalline form of a serine salt of Compound (I) which has characteristic peaks in the powder X-ray diffraction (XRPD) pattern at values of two theta (° 2θ) of 16.3, 17.3, 19.0, 20.7, 22.8, 23.5, 24.8, and 28.2.

In another aspect, the invention features a crystalline form of a serine salt of Compound (I) which has characteristic peaks in the powder X-ray diffraction (XRPD) pattern at values of two theta (° 2θ) of 16.3, 17.3, 18.5, 19.0, 20.7, 21.2, 21.7, 22.0, 22.8, 23.5, 24.8, 26.1, 27.0, and 28.2.

Figure 5:
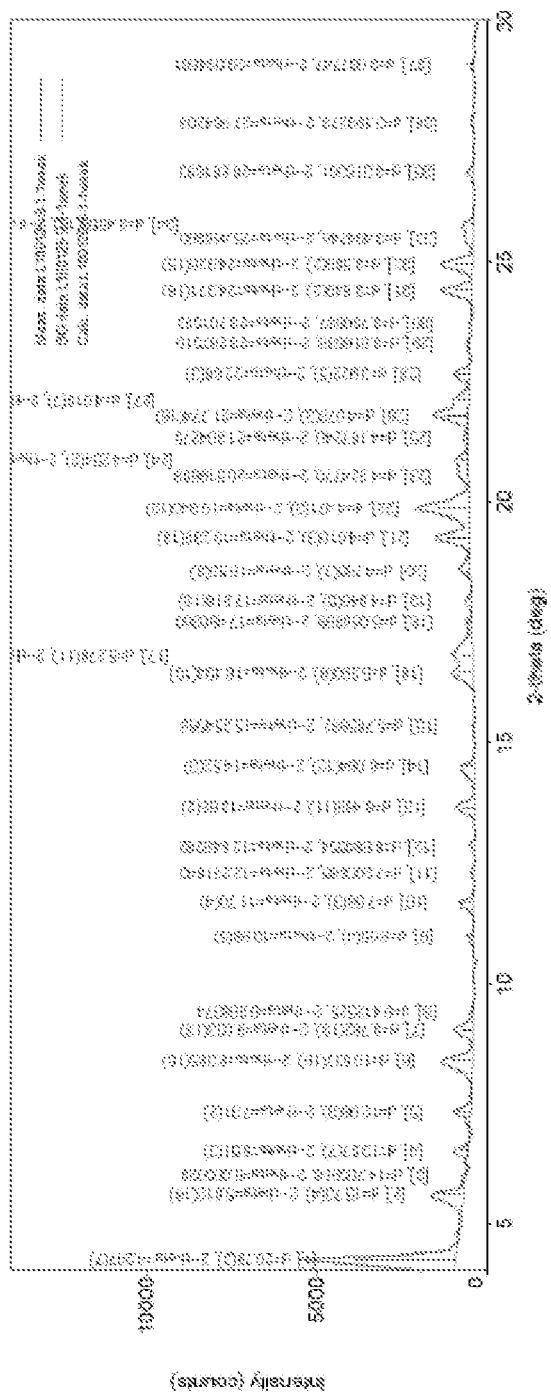
FIG. 5 depicts an XRPD pattern of a tosylate salt of Compound (I).
Figure 6:
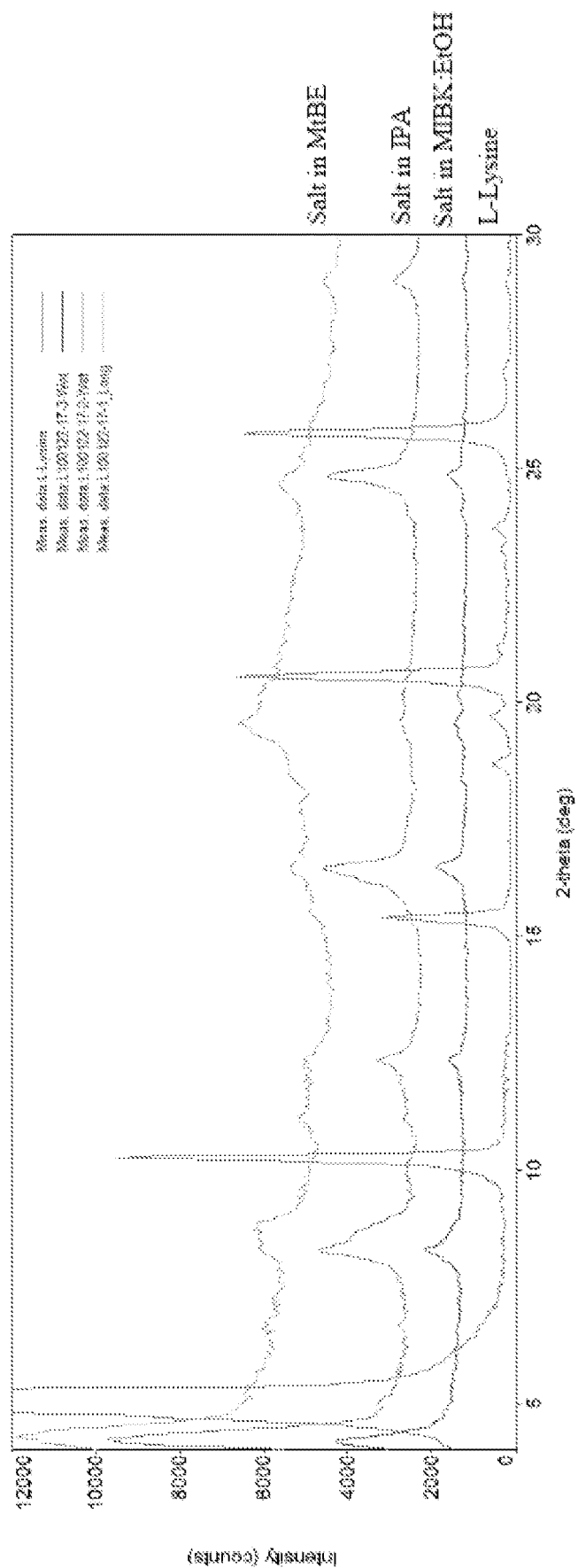
FIG. 6 depicts XRPD patterns of solids produced using L-lysine as CI, compared with the pattern of L-lysine itself.
Figure 7:
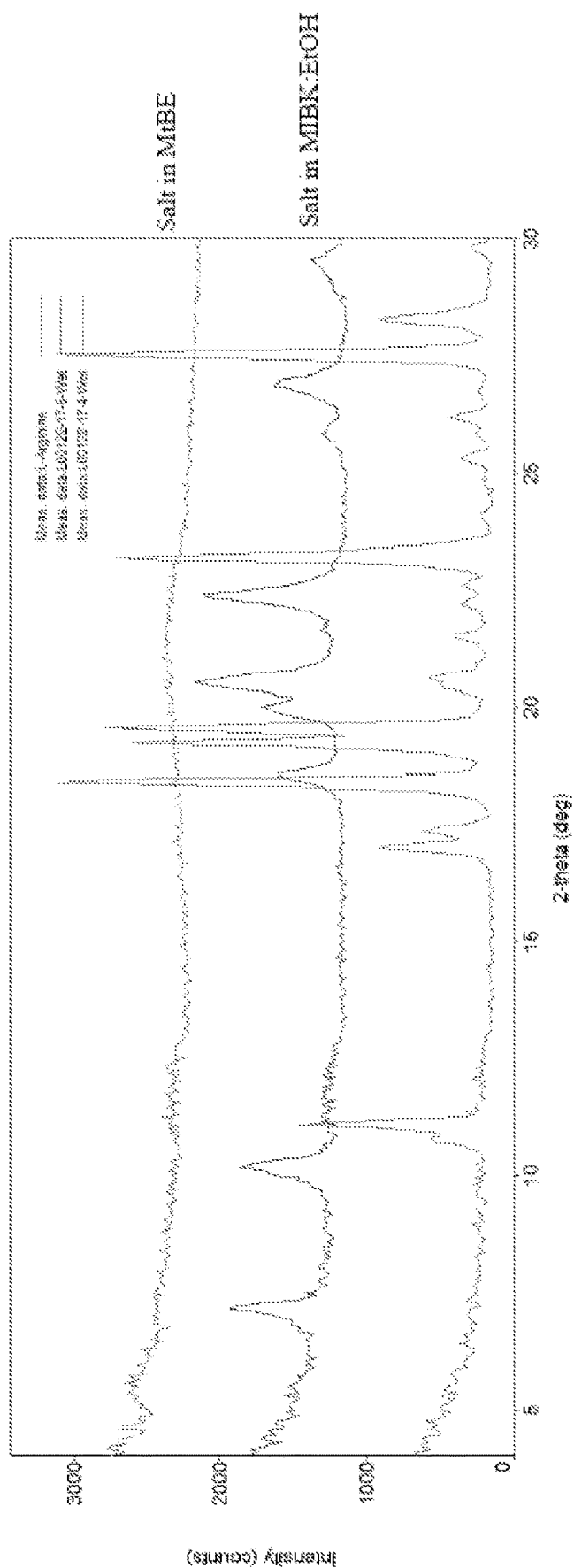
FIG. 7 depicts XRPD patterns of solids produced with L-arginine as CI, showing that the solid in EtOH:MIBK (1:1) is unique.

In yet another aspect, the invention features a crystalline form of a tosylate salt of Compound (I) which has characteristic peaks in the powder X-ray diffraction (XRPD) pattern as shown in FIG. 5.

In yet another aspect, the invention features a crystalline form of a tosylate salt of Compound (I) which has characteristic peaks in the powder X-ray diffraction (XRPD) pattern as shown in Table 36.

In another aspect, the invention features a crystalline form of a tosylate salt of Compound (I) which has characteristic peaks in the powder X-ray diffraction (XRPD) pattern at values of two theta (° 2θ) of 4.2, 5.6, 8.4, 19.2, 19.8, 21.8, 24.4, and 24.9.

In another aspect, the invention features a crystalline form of a tosylate salt of Compound (I) which has characteristic peaks in the powder X-ray diffraction (XRPD) pattern at values of two theta (° 2θ) of 4.2, 5.6, 7.3, 8.4, 9.0, 13.7, 16.4, 16.8, 19.2, 19.8, 21.8, 22.1, 22.7, 24.4, and 24.9.

The term "substantially pure" as used herein, refers to a crystalline polymorph that is greater than 90% pure, meaning that contains less than 10% of any other compound, including the corresponding amorphous compound or an alternative polymorph of the crystalline salt. Preferably, the crystalline polymorph is greater than 95% pure, or even greater than 98% pure.

In one embodiment, the present invention features a crystalline form of Compound (I) which has characteristic peaks in the powder X-ray diffraction (XRPD) pattern as shown in any one of FIGS. 1-5 and which is substantially pure. For example, the crystalline form can be at least 90% pure, preferably at least 95% pure, or more preferably at least 98%.

In another embodiment, the present invention features a crystalline form of Compound (I) which has characteristic peaks in the powder X-ray diffraction (XRPD) pattern at values of two theta (° 2θ) as shown in any one of Tables 32-36 and which is substantially pure. For example, the crystalline form can be at least 90% pure, preferably at least 95% pure, or more preferably at least 98%.

Methods of Making the Crystalline Salts

In certain embodiments, the invention relates to a method for the preparation of a crystalline salt of a compound having the structure of formula (I), comprising a) providing a freebase mixture of a compound of formula (I) in a first organic solvent; b) contacting the freebase mixture with a reagent solution comprising an acid and optionally a second organic solvent under conditions sufficient to form a mixture comprising a salt of the compound of formula (I); and c) crystallizing the salt of the compound of formula (I) from the mixture comprising a salt of the compound of formula (I).

In certain embodiments, the invention relates to a method for the preparation of a crystalline salt of a compound having the structure of formula (I), comprising a) providing a first salt mixture of a compound of formula (I) in a first organic solvent; b) contacting the first salt mixture with a reagent solution comprising an acid and optionally a second organic solvent under conditions sufficient to form a mixture comprising a second salt of the compound of formula (I); and c) crystallizing the second salt of the compound of formula (I) from the mixture comprising a second salt of the compound of formula (I).

In certain embodiments, the invention relates to a method for the preparation of a crystalline salt of a compound having the structure of formula (I), comprising a) providing a first mixture comprising a protected form of a compound of formula (I) in a first organic solvent; b) contacting the first mixture with a reagent solution comprising an acid and optionally a second organic solvent under conditions sufficient to deprotect the protected form of the compound of formula (I) and to form a mixture comprising a salt of the compound of formula (I); and c) crystallizing the salt of the compound of formula (I) from the mixture comprising a salt of the compound of formula (I).

In certain embodiments, the mixture comprising a salt of the compound of formula (I) formed in step b) is a solution. In certain embodiments, the mixture formed in step b) is a slurry or a suspension.

In certain embodiments, the mixture comprising the salt of the compound of formula (I) is a solution, and the step of crystallizing the salt from the mixture comprises bringing the solution to supersaturation to cause the salt of the compound of formula (I) to precipitate out of solution.

In certain embodiments, bringing the mixture comprising the salt of a compound of formula (I) to supersaturation comprises the slow addition of an anti-solvent, such as heptanes, hexanes, ethanol, or another polar or non-polar liquid miscible with the organic solvent, allowing the solution to cool (with or without seeding the solution), reducing the volume of the solution, or any combination thereof. In certain embodiments, bringing the mixture comprising the salt of a compound of formula (I) to supersaturation comprises adding an anti-solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, the preparation method further comprises isolating the salt crystals, e.g. by filtering the crystals, by decanting fluid from the crystals, or by any other suitable separation technique. In further embodiments, the preparation method further comprises washing the crystals.

In certain embodiments, the preparation method further comprises inducing crystallization. The method can also comprise the step of drying the crystals, for example under reduced pressure. In certain embodiments, inducing precipitation or crystallization comprises secondary nucleation, wherein nucleation occurs in the presence of seed crystals or interactions with the environment (crystallizer walls, stirring impellers, sonication, etc.).

In certain embodiments, the freebase mixture of a compound of formula (I) in a first organic solvent is a slurry. In certain embodiments, the freebase mixtures of a compound of formula (I) in a first organic solvent is a solution.

In certain embodiments, the first organic solvent and the second organic solvent, if present, comprise acetone, anisole, methanol, 1-butanol, 2-butanone, iso-butanol, tert-butanol, sec-butanol, cyclopentyl methylester (CPME), benzotrifluoride (BTF), 1-propanol, 2-propanol (IPA), water, dichloromethane, anisole, acetonitrile, ethylene glycol, tert-butyl methyl ether (t-BME), DMSO, ethylene glycol, toluene, tetrahydrofuran (THF), heptane, acetonitrile, N,N-dimethylacetamide (DMA), dimethylformamide (DMF), dimethylsulfoxide (DMSO), 1,4-dioxane, 2-ethoxy ethanol, heptane, isopropyl acetate, methyl acetate, 2-methyl THF, methyl isobutyl ketone (MIBK), 1-propanol, ethanol, ethyl acetate, hexanes, methyl acetate, isopropyl acetate, methylethyl ketone, 1,4-dioxane, methyl cyclohexane, N-methyl-2-pyrrolidone (NMP), or any combination thereof.

In certain embodiments, the first organic solvent and the second organic solvent, if present, are the same. In alterative embodiments, the first organic solvent and the second organic solvent, if present, are different.

In certain embodiments, washing the crystals comprises washing with a liquid selected from anti-solvent, acetonitrile, ethanol, heptanes, hexanes, methanol, tetrahydrofuran, toluene, water, or a combination thereof. As used herein, "anti-solvent" means a solvent in which the salt crystals are insoluble, minimally soluble, or partially soluble. In practice, the addition of an anti-solvent to a solution in which the salt crystals are dissolved reduces the solubility of the salt crystals in solution, thereby stimulating precipitation of the salt. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene. In certain embodiments, the anti-solvent is ethanol.

In certain embodiments, washing the crystals comprises washing the crystalline compound of formula (I) with a solvent or a mixture of one or more solvents, which are described above. In certain embodiments, the solvent or mixture of solvents is cooled prior to washing.

Pharmaceutical Compositions

In certain embodiments, the present invention relates to pharmaceutical compositions comprising a crystalline compound or salt of a compound of formula (I) and one or more pharmaceutically acceptable excipients.

Exemplary pharmaceutically acceptable excipients are presented herein, and include, for example binders, disintegrating agents, lubricants, corrigents, solubilizing agents, suspension aids, emulsifying agents, coating agents, cyclodextrins, and/or buffers. Although the dosage could vary depending on the symptoms, age and body weight of the patient, the nature and severity of the disorder to be treated or prevented, the route of administration and the form of the drug, in general, a daily dosage of from 0.01 to 3000 mg of the Compound (I)s recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

In certain embodiments, the individual to which the composition is administered is a mammal such as a human, or a non-human mammal. When administered to an animal, such as a human, the composition or the Compound (I)s preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is sterile and pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop, through ophthalmic mucous membrane administration or penetration of the corneal epithelium.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextran, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the compounds. These salts can be prepared in situ during the final isolation and purification of the compounds, or by separately reacting a purified Compound (I)n its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. Preparation of the crystalline salts is detailed in the Examples, below (See, for example, Berge et al. (1977) "Pharmaceutical Salts", J. Pharm. Sci. 66: 1-19.).

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound. These salts can likewise be prepared in situ during the final isolation and purification of the compound, or by separately reacting the purified Compound (I)n its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Other representative salts include the copper and iron salts. Representative organic amines useful for the formation of base addition salts include ethylamine, diethylamine, ethylenediamine, ethanolamine, diethanolamine, piperazine, and the like (see, for example, Berge et al., supra).

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually or buccally); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896 (all of which are incorporated by reference), as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. Compositions or compounds may also be administered as a bolus, electuary or paste.

To prepare solid dosage forms for oral administration capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin, microcrystalline cellulose, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the compositions of the present invention can also include adjuvants such as wetting agents, lubricants, emulsifying and suspending agents such as sodium lauryl sulfate and magnesium stearate, or sweetening, flavoring, coloring, perfuming, preservative, or antioxidant agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively, or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, vaginal rings for sustained-release (e.g., polymeric vaginal rings) creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compounds described herein can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the present invention to the body. Such dosage forms can be made by dissolving or dispersing the active Compound (I)n the proper medium. Absorption enhancers can also be used to increase the flux of the compound across the skin. The rate of such flux can be controlled by either providing a rate controlling membrane or dispersing the Compound (I)n a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of all of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, intravitreal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, metacresol, benzoic acid and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous, intravitreal or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

These compounds may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compounds, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of metabolism or excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1 single or 2-4 divided doses. Each divided dose may contain the same or different compounds of the invention.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882).

In general, a suitable daily dose of an active compound used in the compositions and methods of the invention will be that amount of the compound that is the lowest dose effective to produce a therapeutic effect or the maximally tolerated dose. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second Compound (I)s administered while the previously administered therapeutic Compound (I)s still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn, Cu, Fe or other metal salts.

The pharmaceutically acceptable acid addition salts can also exist as various solvates, such as with water, methanol, ethanol, dimethylformamide, dichloromethane, acetonitrile, acetone, ethyl acetate, cyclopentyl methyl ether and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLES

Materials and Methods

X-Ray Diffraction

Powder x-ray diffraction experiments were performed on a Rigaku MiniFlex 600 equipped with a Cu Kα radiation source (wavelength of x-rays 1.54 Å) and a scintillation detector. Samples were prepared on Si zero-return wafers. Regular shorter scans were performed from 2θ 4 to 30 degrees over a step size of 0.05 degrees over a span of 5 minutes while high resolution scans are from 2θ of 4 to 40 degrees, with step size 0.05 degrees over thirty minutes with cathode ray tube voltage and current 40 kV and 15 mA, respectively.

Thermogravimetric Analysis (TGA)

Thermogravimetric analysis was performed on a Mettler Toledo TGA/DSC3+.

Differential Scanning Calorimetry (DSC)

Differential scanning calorimetry was performed on a Mettler Toledo TGA/DSC3+. A heating rate of 10° C./min was employed and the scan was performed over a range of 30–250° C. or from 30 to 300° C. A typical sample size of about 6-8 mg was used. A standalone DSC 3+ was also used to obtain thermograms of samples when the sample size was small.

1H Nuclear Magnetic Resonance Spectroscopy (1H NMR)

1H-NMR spectroscopic experiments were performed on a Bruker Avance 300 MHz spectrometer.

High Performance Liquid Chromatography (HPLC)

HPLC analysis was performed on a Hitachi HPLC equipped with DAD detector. The HPLC column was C18 5μ 100A, 4.6 mm×250 mm was used. The concentration was monitored at 220 nm wavelength.

Agilent 1220 HPLC equipped with a single wavelength uv detector was used to analyze part of the samples. The details of the HPLC analyses were:

Mobile Phase A—0.05% TFA in Water
Mobile Phase B—0.05% TFA in ACN
Diluent—Water:ACN (9:1 Vol)
Column—Waters XSelect CSH C18, 3.5 μm, 4.6×150 mm
Flow rate—1 mL/min
Injection volume—10 μL
Column temperature—30° C.

The Gradient method for the HPLC run is given below in Table 1.

TABLE 1

Gradient method for HPLC

| Time (min) | Mobile Phase A (%) | Mobile Phase B (%) |
|---|---|---|
| 0.0 | 95 | 5 |
| 1.0 | 95 | 5 |
| 16.0 | 80 | 20 |
| 21.0 | 50 | 50 |
| 26.0 | 10 | 90 |
| 28.0 | 10 | 90 |
| 28.1 | 95 | 5 |
| 36.0 | 95 | 5 |

Example 1. Primary Salt Screen on SBT-020

Initial salt screening was performed on SBT-020 di-Acetate with 15 different counter-ions to identify alternate salts. The counter-ions that were selected for this screening are shown in Table 2. The pKa of all the counter-ions tested was less than the pKa of Acetic acid which is 4.75. This was an indication that all the counter-ions studied can replace Acetic acid and form a salt with SBT-020.

TABLE 2

Counter-ions studied during the initial salt screening of SBT-020

| Counter ions identifier No. | Counter-ions under consideration | pKa1 | pKa2 | pKa3 |
|---|---|---|---|---|
| 1 | Benzene sulfonic acid | −2.8 | | |
| 2 | Benzoic acid | 4.19 | | |
| 3 | Citric acid | 3.128 | 4.761 | 6.396 |
| 4 | Fumaric acid | 3.03 | 4.54 | |
| 5 | Hydrobromic acid | −8 | | |
| 6 | Hydrochloric acid | −7.7 | | |
| 7 | Malic acid | 3.4 | 5.2 | |
| 8 | Maleic acid | 1.93 | 6.58 | |
| 9 | Methanesulfonic acid | −1.2 | | |
| 10 | Salicylic acid | 2.98 | | |
| 11 | Sulfuric acid | 1.92 | | |
| 12 | Succinic acid | 4.03 | 5.28 | |
| 13 | Tartaric acid | 3 | 4.4 | |
| 14 | Toluene sulfonic acid | −2.8 | | |
| 15 | Phosphoric acid | 2.15 | 7.09 | 12.32 |

Procedure Followed for the Initial Salt Screening

~25-30 mg of SBT-020 was weighed in 2 mL vials

~2.5 Equivalents of the respective counter-ion was added to each of the respective vials. If the counter-ion is liquid, it is added after the addition of process solvent ~15 V of process solvent was added to each of the respective vials The vials were stirred at RT for ~10 minutes and were heated to 45° C.

The vials were stirred at 45° C. for ~2 hours and observations were made on the appearance and behavior of the system. The vials were cooled to RT and were left stirring at RT over the weekend.

The system in which good flowable slurry was observed, were filtered under the flow of N2 and were subjected to XRPD analysis. Vials in which gumming was observed, were evaporated and re-slurried in the same process solvent.

Solids with unique patterns (in the case of crystalline solids) were dried and XRPD performed again. These dry solids were subjected to TGA/DSC analysis and subjected to humidity exposure for stability.

Based on these observations, the counter-ions along with the solvent systems were selected for scale-up The mass of the API used and the amount of counter-ion added are shown in Table 3. The cells highlighted in grey are the counter-ions that were in solutions. The counter-ion solutions were diluted to 10% of their strength in the respective solvent/solvent system in which the salt formation will be evaluated. The value provided is the amount added in μL that is calculated based on the 10% dilution.

TABLE 3

Amount of API and the counter-ions added during the initial salt screening

| Vial # | mass API (g) | Solvent/Solvent System | Counter ion | CI molar mass | CI purity | # eq. expected | CI mass expected (g) | CI mass added (g) | CI #eq. added |
|---|---|---|---|---|---|---|---|---|---|
| 122-3-1 | 0.0251 | MeOH | Benzenesulfonic Acid | 158.17 | 0.98 | 2.5 | 0.0139 | 0.0143 | 2.56 |
| 122-3-2 | 0.025 | IPA | Benzenesulfonic Acid | 158.17 | 0.98 | 2.5 | 0.0139 | 0.0141 | 2.54 |
| 122-3-3 | 0.0249 | EtOH:MeOAc (1:1) | Benzenesulfonic Acid | 158.17 | 0.98 | 2.5 | 0.0138 | 0.0160 | 2.89 |
| 122-3-4 | 0.0263 | EtOH:MIBK (1:1) | Benzenesulfonic Acid | 158.17 | 0.98 | 2.5 | 0.0146 | 0.0158 | 2.70 |
| 122-3-5 | 0.026 | ACN:Water (98:2) | Benzenesulfonic Acid | 158.17 | 0.98 | 2.5 | 0.0144 | 0.0167 | 2.89 |
| 122-3-6 | 0.0276 | MeOH | Benzoic Acid | 122.12 | 0.995 | 2.5 | 0.0117 | 0.0132 | 2.83 |
| 122-3-7 | 0.0257 | IPA | Benzoic Acid | 122.12 | 0.995 | 2.5 | 0.0109 | 0.0110 | 2.53 |
| 122-3-8 | 0.0273 | EtOH:MeOAc (1:1) | Benzoic Acid | 122.12 | 0.995 | 2.5 | 0.0115 | 0.0124 | 2.69 |
| 122-3-9 | 0.0262 | EtOH:MIBK (1:1) | Benzoic Acid | 122.12 | 0.995 | 2.5 | 0.0111 | 0.0110 | 2.48 |
| 122-3-10 | 0.0273 | ACN:Water (98:2) | Benzoic Acid | 122.12 | 0.995 | 2.5 | 0.0115 | 0.0113 | 2.45 |
| 122-3-11 | 0.0253 | MeOH | Citric Acid | 192.124 | 0.995 | 2.5 | 0.0168 | 0.0181 | 2.69 |
| 122-3-12 | 0.0252 | IPA | Citric Acid | 192.124 | 0.995 | 2.5 | 0.0167 | 0.0166 | 2.48 |
| 122-3-13 | 0.0254 | EtOH:MeOAc (1:1) | Citric Acid | 192.124 | 0.995 | 2.5 | 0.0169 | 0.0164 | 2.43 |
| 122-3-14 | 0.0272 | EtOH:MIBK (1:1) | Citric Acid | 192.124 | 0.995 | 2.5 | 0.0181 | 0.0196 | 2.71 |
| 122-3-15 | 0.0277 | ACN:Water (98:2) | Citric Acid | 192.124 | 0.99 | 2.5 | 0.0184 | 0.0187 | 2.54 |
| 122-3-16 | 0.0278 | MeOH | Fumaric Acid | 116.07 | 0.99 | 2.5 | 0.0112 | 0.0111 | 2.47 |
| 122-3-17 | 0.0274 | IPA | Fumaric Acid | 116.07 | 0.99 | 2.5 | 0.0111 | 0.0124 | 2.80 |
| 122-3-18 | 0.0254 | EtOH:MeOAc (1:1) | Fumaric Acid | 116.07 | 0.99 | 2.5 | 0.0102 | 0.0110 | 2.68 |
| 122-3-19 | 0.0254 | EtOH:MIBK (1:1) | Fumaric Acid | 116.07 | 0.99 | 2.5 | 0.0102 | 0.0123 | 3.00 |
| 122-3-20 | 0.0269 | ACN:Water (98:2) | Fumaric Acid | 116.07 | 0.99 | 2.5 | 0.0109 | 0.0112 | 2.58 |
| 122-3-21 | 0.0267 | MeOH | Hydrobromic Acid | 80.91 | 0.48 | 2.5 | 0.0155 | 104.0 | 2.50 |
| 122-3-22 | 0.0255 | IPA | Hydrobromic Acid | 80.91 | 0.48 | 2.5 | 0.0148 | 99.3 | 2.50 |
| 122-3-23 | 0.0248 | EtOH:MeOAc (1:1) | Hydrobromic Acid | 80.91 | 0.48 | 2.5 | 0.0144 | 96.6 | 2.50 |
| 122-3-24 | 0.0258 | EtOH:MIBK (1:1) | Hyrobromic Acid | 80.91 | 0.48 | 2.5 | 0.0150 | 100.5 | 2.50 |
| 122-3-25 | 0.0264 | ACN:Water (98:2) | Hydrobromic Acid | 80.91 | 0.48 | 2.5 | 0.0153 | 102.8 | 2.50 |
| 122-3-26 | 0.0257 | MeOH | Hydrochloric Acid | 36.46094 | 0.365 | 2.5 | 0.0088 | 176.9 | 2.50 |
| 122-3-27 | 0.0265 | IPA | Hydrochloric Acid | 36.46094 | 0.365 | 2.5 | 0.0091 | 182.4 | 2.50 |
| 122-3-28 | 0.0274 | EtOH:MeOAc (1:1) | Hydrochloric Acid | 36.46094 | 0.365 | 2.5 | 0.0094 | 188.6 | 2.50 |
| 122-3-29 | 0.0271 | EtOH:MIBK (1:1) | Hydrochloric Acid | 36.46094 | 0.365 | 2.5 | 0.0093 | 186.5 | 2.50 |
| 122-3-30 | 0.0269 | ACN:Water (98:2) | Hydrochloric Acid | 36.46094 | 0.365 | 2.5 | 0.0092 | 185.2 | 2.50 |
| 122-3-31 | 0.0278 | MeOH | Malic Acid | 134.0874 | 1 | 2.5 | 0.0128 | 0.0128 | 2.49 |
| 122-3-32 | 0.0285 | IPA | Malic Acid | 134.0874 | 1 | 2.5 | 0.0132 | 0.0137 | 2.60 |
| 122-3-33 | 0.0276 | EtOH:MeOAc (1:1) | Malic Acid | 134.0874 | 1 | 2.5 | 0.0127 | 0.0171 | 3.36 |
| 122-3-34 | 0.0264 | EtOH:MIBK (1:1) | Malic Acid | 134.0874 | 1 | 2.5 | 0.0122 | 0.0122 | 2.50 |
| 122-3-35 | 0.0277 | ACN:Water (98:2) | Malic Acid | 134.0874 | 1 | 2.5 | 0.0128 | 0.0129 | 2.52 |
| 122-3-36 | 0.0273 | MeOH | Maleic Acid | 116.07 | 0.99 | 2.5 | 0.0110 | 0.0114 | 2.59 |
| 122-3-37 | 0.0255 | IPA | Maleic Acid | 116.07 | 0.99 | 2.5 | 0.0103 | 0.0102 | 2.48 |
| 122-3-38 | 0.0262 | EtOH:MeOAc (1:1) | Maleic Acid | 116.07 | 0.99 | 2.5 | 0.0106 | 0.0112 | 2.65 |
| 122-3-39 | 0.0296 | EtOH:MIBK (1:1) | Maleic Acid | 116.07 | 0.99 | 2.5 | 0.0119 | 0.0116 | 2.43 |
| 122-3-40 | 0.0287 | ACN:Water (98:2) | Maleic Acid | 116.07 | 0.99 | 2.5 | 0.0116 | 0.0116 | 2.50 |
| 122-3-41 | 0.0278 | MeOH | Methanesulfonic Acid | 96.1 | 0.98 | 2.5 | 0.0094 | 63.4 | 2.50 |

TABLE 3-continued

Amount of API and the counter-ions added during the initial salt screening

| Vial # | mass API (g) | Solvent/Solvent System | Counter ion | CI molar mass | CI purity | # eq. expected | CI mass expected (g) | CI mass added (g) | CI #eq. added |
|---|---|---|---|---|---|---|---|---|---|
| 122-3-42 | 0.0251 | IPA | Methanesulfonic Acid | 96.1 | 0.98 | 2.5 | 0.0085 | 57.2 | 2.50 |
| 122-3-43 | 0.0271 | EtOH:MeOAc (1:1) | Methanesulfonic Acid | 96.1 | 0.98 | 2.5 | 0.0091 | 61.8 | 2.50 |
| 122-3-44 | 0.0265 | EtOH:MIBK (1:1) | Methanesulfonic Acid | 96.1 | 0.98 | 2.5 | 0.0089 | 60.4 | 2.50 |
| 122-3-45 | 0.0266 | ACN:Water (98:2) | Methanesulfonic Acid | 96.1 | 0.98 | 2.5 | 0.0090 | 60.6 | 2.50 |
| 122-3-46 | 0.0266 | MeOH | Salicylic Acid | 138.121 | 0.99 | 2.5 | 0.0128 | 0.0136 | 2.66 |
| 122-3-47 | 0.0268 | IPA | Salicylic Acid | 138.121 | 0.99 | 2.5 | 0.0129 | 0.0174 | 3.38 |
| 122-3-48 | 0.0264 | EtOH:MeOAc (1:1) | Salicylic Acid | 138.121 | 0.99 | 2.5 | 0.0127 | 0.0137 | 2.70 |
| 122-3-49 | 0.0268 | EtOH:MIBK (1:1) | Salicylic Acid | 138.121 | 0.99 | 2.5 | 0.0129 | 0.0149 | 2.89 |
| 122-3-50 | 0.0259 | ACN:Water (98:2) | Salicylic Acid | 138.121 | 0.99 | 2.5 | 0.0124 | 0.0134 | 2.69 |
| 122-3-51 | 0.025 | MeOH | Sulfuric Acid | 98.079 | 0.95 | 2.5 | 0.0089 | 48.3 | 2.50 |
| 122-3-52 | 0.0251 | IPA | Sulfuric Acid | 98.079 | 0.95 | 2.5 | 0.0089 | 48.5 | 2.50 |
| 122-3-53 | 0.0265 | EtOH:MeOAc (1:1) | Sulfuric Acid | 98.079 | 0.95 | 2.5 | 0.0094 | 51.2 | 2.50 |
| 122-3-54 | 0.0257 | EtOH:MIBK (1:1) | Sulfuric Acid | 98.079 | 0.95 | 2.5 | 0.0091 | 49.6 | 2.50 |
| 122-3-55 | 0.0275 | ACN:Water (98:2) | Sulfuric Acid | 98.079 | 0.95 | 2.5 | 0.0098 | 53.1 | 2.50 |
| 122-3-56 | 0.0249 | MeOH | Succinic Acid | 118.09 | 0.99 | 2.5 | 0.0102 | 0.0119 | 2.91 |
| 122-3-57 | 0.025 | IPA | Succinic Acid | 118.09 | 0.99 | 2.5 | 0.0103 | 0.0113 | 2.75 |
| 122-3-58 | 0.0262 | EtOH:MeOAc (1:1) | Succinic Acid | 118.09 | 0.99 | 2.5 | 0.0108 | 0.0115 | 2.67 |
| 122-3-59 | 0.0258 | EtOH:MIBK (1:1) | Succinic Acid | 118.09 | 0.99 | 2.5 | 0.0106 | 0.0122 | 2.88 |
| 122-3-60 | 0.0285 | ACN:Water (98:2) | Succinic Acid | 118.09 | 0.99 | 2.5 | 0.0117 | 0.0132 | 2.82 |
| 122-3-61 | 0.0262 | MeOH | Tartatic Acid | 150.87 | 0.999 | 2.5 | 0.0135 | 0.0137 | 2.53 |
| 122-3-62 | 0.0249 | IPA | Tartatic Acid | 150.87 | 0.999 | 2.5 | 0.0129 | 0.0138 | 2.68 |
| 122-3-63 | 0.0249 | EtOH:MeOAc (1:1) | Tartatic Acid | 150.87 | 0.999 | 2.5 | 0.0129 | 0.0131 | 2.54 |
| 122-3-64 | 0.0286 | EtOH:MIBK (1:1) | Tartatic Acid | 150.87 | 0.999 | 2.5 | 0.0148 | 0.0162 | 2.74 |
| 122-3-65 | 0.026 | ACN:Water (98:2) | Tartatic Acid | 150.87 | 0.999 | 2.5 | 0.0134 | 0.0169 | 3.14 |
| 122-3-66 | 0.0262 | MeOH | Tolueme Sulfonic Acid | 172.2 | 0.985 | 2.5 | 0.0158 | 0.0188 | 2.98 |
| 122-3-67 | 0.0273 | IPA | Tolueme Sulfonic Acid | 172.2 | 0.985 | 2.5 | 0.0164 | 0.0183 | 2.79 |
| 122-3-68 | 0.0274 | EtOH:MeOAc (1:1) | Tolueme Sulfonic Acid | 172.2 | 0.985 | 2.5 | 0.0165 | 0.0205 | 3.11 |
| 122-3-69 | 0.0264 | EtOH:MIBK (1:1) | Tolueme Sulfonic Acid | 172.2 | 0.985 | 2.5 | 0.0159 | 0.0172 | 2.71 |
| 122-3-70 | 0.0271 | ACN:Water (98:2) | Tolueme Sulfonic Acid | 172.2 | 0.985 | 2.5 | 0.0163 | 0.0237 | 3.63 |
| 122-3-71 | 0.0255 | MeOH | Phosphoric Acid | 98 | 0.98 | 2.5 | 0.0088 | 53.2 | 2.50 |
| 122-3-72 | 0.0274 | IPA | Phosphoric Acid | 98 | 0.98 | 2.5 | 0.0094 | 57.2 | 2.50 |
| 122-3-73 | 0.027 | EtOH:MeOAc (1:1) | Phosphoric Acid | 98 | 0.98 | 2.5 | 0.0093 | 56.3 | 2.50 |
| 122-3-74 | 0.0252 | EtOH:MIBK (1:1) | Phosphoric Acid | 98 | 0.98 | 2.5 | 0.0087 | 52.6 | 2.50 |
| 122-3-75 | 0.0261 | ACN:Water (98:2) | Phosphoric Acid | 98 | 0.98 | 2.5 | 0.0090 | 54.4 | 2.50 |

Observations were made at 45° C. and after keeping the vials stirring at room temperature for 2 days. These observations were provided in Table 4.

TABLE 4

Observations of from the initial salt screening

| Vial # | mass API (g) | Counter ion | Solvent | Observation at 45 C. | Observation at RT after weekend slurry |
|---|---|---|---|---|---|
| 122-3-1 | 0.0251 | Benzenesulfonic acid | MeOH | Clear solution | Clear solution |
| 122-3-2 | 0.025 | Benzenesulfonic acid | IPA | Clear solution, slight gumming | gum formation |
| 122-3-3 | 0.0249 | Benzenesulfonic acid | EtOH:MeOAc (1:1) | Cloudy solution | Cloudy solution |
| 122-3-4 | 0.0263 | Benzenesulfonic acid | EtOH:MIBK (1:1) | Clear solution, minor gelling on the bottom | Clear solution, minor gelling on the bottom |
| 122-3-5 | 0.026 | Benzenesulfonic acid | ACN:Water (98:2) | Gelling on the bottom | Gelling on the bottom |
| 122-3-6 | 0.0276 | Benzoic Acid | MeOH | Clear solution | Clear solution |
| 122-3-7 | 0.0257 | Benzoic Acid | IPA | Clear solution | Clear solution |
| 122-3-8 | 0.0273 | Benzoic Acid | EtOH:MeOAc (1:1) | Clear solution | Clear solution |
| 122-3-9 | 0.0252 | Benzoic Acid | EtOH:MIBK (1:1) | Clear solution | Clear solution |
| 122-3-10 | 0.0273 | Benzoic Acid | ACN:Water (98:2) | Cloudy solution, minor gelling | Clear solution, minor gelling on the bottom |
| 122-3-11 | 0.0253 | Citric Acid | MeOH | Clear solution | Clear solution, minor gelling on the bottom |
| 122-3-12 | 0.0252 | Citric Acid | IPA | Freezing | Slurry |

TABLE 4-continued

Observations of from the initial salt screening

| Vial # | mass API (g) | Counter ion | Solvent | Observation at 45 C. | Observation at RT after weekend slurry |
|---|---|---|---|---|---|
| 122-3-13 | 0.0254 | Citric Acid | EtOH:MeOAc (1:1) | Gumming | Gumming, thin slurry upon vortexing |
| 122-3-14 | 0.0272 | Citric Acid | EtOH:MIBK (1:1) | Gumming/Freezing | Slurry, slight gumming |
| 122-3-15 | 0.0277 | Citric Acid | ACN:Water (98:2) | Undissolved solid that gummed | Undissolved solid that gummed |
| 122-3-16 | 0.0278 | Fumaric Acid | MeOH | Clear solution | Clear solution |
| 122-3-17 | 0.0274 | Fumaric Acid | IPA | Slurry, gumming | Thick slurry |
| 122-3-18 | 0.0254 | Fumaric Acid | EtOH:MeOAc (1:1) | Gumming, gelling on the bottom | Gumming |
| 122-3-19 | 0.0254 | Fumaric Acid | EtOH:MIBK (1:1) | Gumming | Gumming |
| 123-3-20 | 0.0269 | Fumaric Acid | ACN:Water (98:2) | Undissolved solid/gumming | undissolved solid/gumming |
| 122-3-21 | 0.0267 | Hydrobromic Acid | MeOH | Clear solution | Clear solution |
| 122-3-22 | 0.0255 | Hydrobromic Acid | IPA | Slight gumming | Gumming in the bottom |
| 122-3-23 | 0.0248 | Hydrobromic Acid | EtOH:MeOAc (1:1) | Clear solution/slight gumming | Clear solution/slight gumming |
| 122-3-24 | 0.0258 | Hydrobromic Acid | EtOH:MIBK (1:1) | Clear solution/slight gumming | Clear solution |
| 122-3-25 | 0.0264 | Hydrobromic Acid | ACN:Water (98:2) | Gumming on the bottom | Clear solution/slight gumming |
| 122-3-26 | 0.0257 | Hydrochloric Acid | MeOH | Clear Solution | Clear Solution |
| 122-3-27 | 0.0265 | Hydrochloric Acid | IPA | Thick Slurry | Slurry |
| 122-3-28 | 0.0274 | Hydrochloric Acid | EtOH:MeOAc (1:1) | Gumming | Clear Solution/Gumming |
| 122-3-29 | 0.0271 | Hydrochloric Acid | EtOH:MIBK (1:1) | Gumming | Gumming |
| 122-3-30 | 0.0269 | Hydrochloric Acid | ACN:Water (98:2) | Undissolved solid/gumming | Undissolved solid/gumming |
| 122-3-31 | 0.0278 | Malic Acid | MeOH | Clear solution | Clear solution |
| 122-3-32 | 0.0285 | Malic Acid | IPA | Gumming | Slight gum/thick slurry |
| 122-3-33 | 0.0276 | Malic Acid | EtOH:MeOAc (1:1) | Gumming | Gumming |
| 122-3-34 | 0.0264 | Malic Acid | EtOH:MIBK (1:1) | Gumming | Gumming |
| 122-3-35 | 0.0277 | Malic Acid | ACN:Water (98:2) | Undissolved solid/gumming | Undissolved solid/gumming |
| 122-3-36 | 0.0273 | Maleic Acid | MeOH | Clear Solution | Clear Solution |
| 122-3-37 | 0.0259 | Maleic Acid | IPA | Clear solution/gumming | Clear Solution |
| 122-3-38 | 0.0262 | Maleic Acid | EtOH:MeOAc (1:1) | Cloudy Solution | Cloudy Solution |
| 122-3-39 | 0.0287 | Maleic Acid | EtOH:MIBK (1:1) | Clear solution/slight gumming | Clear solution/slight gumming |
| 122-3-40 | 0.0296 | Maleic Acid | ACN:Water (98:2) | Clear solution/slight gumming | Clear solution/slight gumming |
| 122-3-41 | 0.0278 | Methanesulfonic Acid | MeOH | Clear Solution | Clear Solution |
| 122-3-42 | 0.0251 | Methanesulfonic Acid | IPA | Slurry, slight gumming | Slurry, slight gumming |
| 122-3-43 | 0.0271 | Methanesulfonic Acid | EtOH:MeOAc (1:1) | Gum on the bottom | Clear solution/slight gumming |
| 122-3-44 | 0.0265 | Methanesulfonic Acid | EtOH:MIBK (1:1) | Gum on the bottom | Gum on the bottom |
| 122-3-45 | 0.0266 | Methanesulfonic Acid | ACN:Water (98:2) | Gum on the bottom | Clear solution/gum on the bottom |
| 122-3-46 | 0.0268 | Salicylic Acid | MeOH | Clear Solution | Clear Solution |
| 122-3-47 | 0.0282 | Salicylic Acid | IPA | Clear Solution | Clear Solution |
| 122-3-48 | 0.0264 | Salicylic Acid | EtOH:MeOAc (1:1) | Clear Solution | Clear Solution |
| 122-3-49 | 0.0268 | Salicylic Acid | EtOH:MIBK (1:1) | Clear Solution | Clear Solution |
| 122-3-50 | 0.0259 | Salicylic Acid | ACN:Water (98:2) | Clear solution/gum on the bottom | Clear solution/gum on the bottom |
| 122-3-51 | 0.025 | Sulfuric Acid | MeOH | Clear Solution | Clear Solution |
| 122-3-52 | 0.0251 | Sulfuric Acid | IPA | Thick slurry/Freezing | Thick flowable slurry |
| 122-3-53 | 0.0265 | Sulfuric Acid | EtOH:MeOAc (1:1) | Clear solution/gum on the bottom | Clear solution/gum on the bottom |
| 122-3-54 | 0.0257 | Sulfuric Acid | EtOH:MIBK (1:1) | Clear solution/gum on the bottom | Clear solution/gum on the bottom |
| 122-3-55 | 0.0275 | Sulfuric Acid | ACN:Water (98:2) | Clear solution/gum on the bottom | Clear solution/gum on the bottom with chuncks |
| 122-3-56 | 0.0249 | Succinic Acid | MeOH | Clear Solution | Clear Solution |
| 122-3-57 | 0.025 | Succinic Acid | IPA | Gum on the bottom | Thin slurry with slight gum |
| 122-3-58 | 0.0262 | Succinic Acid | EtOH:MeOAc (1:1) | Gum on the bottom | Gum on the bottom |
| 122-3-59 | 0.0258 | Succinic Acid | EtOH:MIBK (1:1) | Gum on the bottom | Gum on the bottom |
| 122-3-60 | 0.0285 | Succinic Acid | ACN:Water (98:2) | Clear solution/gum on the bottom | Clear solution/gum on the bottom |

Filtration Followed by XRPD Analysis

The experiments that resulted in good/manageable slurries were filtered and were subjected to XRPD analysis (Table 5). All the solids that were obtained were amorphous.

TABLE 5

The experiments that were filtered in the first attempt

| S. No | Exp. ID (L100-) | CI | Solvent |
|---|---|---|---|
| 1 | 122-3-12 | Citric Acid | IPA |
| 2 | 122-3-14 | Citric Acid | EtOH:MIBK (1:1) |
| 3 | 122-3-17 | Fumaric Acid | IPA |
| 4 | 122-3-27 | Hydrochloric Acid | IPA |
| 5 | 122-3-32 | Malic Acid | IPA |
| 6 | 122-3-42 | Methanesulfonic Acid | IPA |
| 7 | 122-3-52 | Sulfuric Arid | IPA |
| 8 | 122-3-62 | Tartaric Acid | IPA |
| 9 | 122-3-63 | Tartaric Acid | EtOH:MeOAc (1:1) |
| 10 | 122-3-64 | Tartaric Add | EtOH:MIBK (1:1) |

Re-Slurry Experiments

The experiments that were clear solutions/gum as shown in Table 38 were evaporated at 50° C. and under vacuum and were re-slurried in the same initial process solvent. In the case of the vials where the initial salt screening was performed in MeOH, the solids produced through evaporation were re-slurried in MeOAc instead due to very high solubility in MeOH. Microscopy was performed on the small sample from these vials and the solvent was evaporated. The dry solids obtained were re-slurried again in the same set of process solvents. Observations were noted down after the second slurry and Microscopy was performed. The observations are shown in Table 6.

TABLE 6

Observations after the second re-slurry in process solvent

| Vial # | mass API (g) | Counter ion | Solvent | Observation after 2nd Re-slurry |
|---|---|---|---|---|
| 122-3-1 | 0.0251 | Benzenesulfonic acid | MeOH | Thin slurry/gum |
| 122-3-2 | 0.025 | Benzenesulfonic acid | IPA | gum |
| 122-3-3 | 0.0249 | Benzenesulfonic acid | EtOH:MeOAc (1:1) | gum |
| 122-3-4 | 0.0263 | Benzenesulfonic acid | EtOH:MIBK (1:1) | |
| 122-3-5 | 0.026 | Benzenesulfonic acid | ACN:Water (98:2) | gum like solid upon evaporation |
| 122-3-6 | 0.0276 | Benzoic Acid | MeOH | gum like solid upon evaporation |
| 122-3-7 | 0.0257 | Benzoic Acid | IPA | |
| 122-3-8 | 0.0273 | Benzoic Acid | EtOH:MeOAc (1:1) | gum like solid upon evaporation |
| 122-3-9 | 0.0262 | Benzoic Acid | EtOH:MIBK (1:1) | gum like solid upon evaporation |
| 122-3-10 | 0.0273 | Benzoic Acid | ACN:Water (98:2) | gum like solid upon evaporation |
| 122-3-11 | 0.0253 | Citric Acid | MeOH | Slurry |
| 122-3-12 | 0.0252 | Citric Acid | IPA | Filtered |
| 122-3-13 | 0.0254 | Citric Acid | EtOH:MeOAc (1:1) | Thick Slurry, gum on the wall |
| 122-3-14 | 0.0272 | Citric Acid | EtOH:MIBK (1:1) | Filtered |
| 122-3-15 | 0.0277 | Citric Acid | ACN:Water (98:2) | gum |
| 122-3-16 | 0.0278 | Fumaric Acid | MeOH | gum like solid upon evaporation |
| 122-3-17 | 0.0274 | Fumaric Acid | IPA | Filtered |
| 122-3-18 | 0.0254 | Fumaric Acid | EtOH:MeOAc (1:1) | gum |
| 122-3-19 | 0.0254 | Fumaric Acid | EtOH:MIBK (1:1) | Clearer solution, gum on wall |
| 122-3-20 | 0.0269 | Fumaric Acid | ACN:Water (98:2) | Clearer solution, gum on wall |
| 122-3-21 | 0.0267 | Hydrobromic Acid | MeOH | slurry |
| 122-3-22 | 0.0255 | Hydrobromic Acid | IPA | slurry |
| 122-3-23 | 0.0248 | Hydrobromic Acid | EtOH:MeOAc (1:1) | gum |
| 122-3-24 | 0.0258 | Hydrobromic Acid | EtOH:MIBK (1:1) | gum |
| 122-3-25 | 0.0264 | Hydrobromic Acid | ACN:Water (98:2) | gum like solid upon evaporation |
| 122-3-26 | 0.0257 | Hydrochloric Acid | MeOH | thick slurry |
| 122-3-27 | 0.0265 | Hydrochloric Acid | IPA | Filtered |
| 122-3-28 | 0.0274 | Hydrochloric Acid | EtOH:MeOAc (1:1) | gum like solid upon evaporation |
| 122-3-29 | 0.0271 | Hydrochloric Acid | EtOH:MIBK (1:1) | Clearer solution, gum on wall |
| 122-3-30 | 0.0269 | Hydrochloric Acid | ACN:Water (98:2) | gum |
| 122-3-31 | 0.0278 | Malic Acid | MeOH | Slurry, gumming on the wall |
| 122-3-32 | 0.0285 | Malic Acid | IPA | Filtered |
| 122-3-33 | 0.0276 | Malic Acid | EtOH:MeOAc (1:1) | gum like solid upon evaporation |
| 122-3-34 | 0.0264 | Malic Acid | EtOH:MIBK (1:1) | slurry/gum |
| 122-3-35 | 0.0277 | Malic Acid | ACN:Water (98:2) | gum |
| 122-3-36 | 0.0273 | Maleic Acid | MeOH | gum/thin slurry |
| 122-3-37 | 0.0255 | Maleic Acid | IPA | gum like solid upon evaporation |
| 122-3-38 | 0.0262 | Maleic Acid | EtOH:MeOAc (1:1) | gum like solid upon evaporation |
| 122-3-39 | 0.0296 | Maleic Acid | EtOH:MIBK (1:1) | gum like solid upon evaporation |
| 122-3-40 | 0.0287 | Maleic Acid | ACN:Water (98:2) | gum like solid upon evaporation |
| 122-3-41 | 0.0278 | Methanesulforic Acid | MeOH | thick slurry |
| 122-3-42 | 0.0251 | Methanesulforic Acid | IPA | Filtered |
| 122-3-43 | 0.0271 | Methanesulforic Acid | EtOH:MeOAc (1:1) | gum like solid upon evaporation |
| 122-3-44 | 0.0265 | Methanesulforic Acid | EtOH:MIBK (1:1) | gum |
| 122-3-45 | 0.0266 | Methanesulforic Acid | ACN:Water (98:2) | gum like solid upon evaporation |
| 122-3-46 | 0.0266 | Salicylic Acid | MeOH | gum like solid upon evaporation |
| 122-3-47 | 0.0268 | Salicylic Acid | IPA | gum like solid upon evaporation |
| 122-3-48 | 0.0264 | Salicylic Acid | EtOH:MeOAc (1:1) | gum like solid upon evaporation |
| 122-3-49 | 0.0268 | Salicylic Acid | EtOH:MIBK (1:1) | gum like solid upon evaporation |
| 122-3-50 | 0.0259 | Salicylic Acid | ACN:Water (98:2) | gum like solid upon evaporation |
| 122-3-51 | 0.025 | Sulfaric Acid | MeOH | slurry |
| 122-3-52 | 0.0251 | Sulfaric Acid | IPA | Filtered |
| 122-3-53 | 0.0265 | Sulfaric Acid | EtOH:MeOAc (1:1) | gum |
| 122-3-54 | 0.0257 | Sulfaric Acid | EtOH:MIBK (1:1) | Clearer solution, gum on wall |
| 122-3-55 | 0.0275 | Sulfaric Acid | ACN:Water (98:2) | gum |
| 122-3-56 | 0.0249 | Succinic Acid | MeOH | gum like solid upon evaporation |
| 122-3-57 | 0.025 | Succinic Acid | IPA | slurry |
| 122-3-58 | 0.0262 | Succinic Acid | EtOH:MeOAc (1:1) | gum |
| 122-3-59 | 0.0258 | Succinic Acid | EtOH:MIBK (1:1) | gum |
| 122-3-60 | 0.0285 | Succinic Acid | ACN:Water (98:2) | gum |
| 122-3-61 | 0.0262 | Tartaric Acid | MeOH | gum like solid upon evaporation |
| 122-3-62 | 0.0249 | Tartaric Acid | IPA | Filtered |
| 122-3-63 | 0.0249 | Tartaric Acid | EtOH:MeOAc (1:1) | Filtered |
| 122-3-64 | 0.0286 | Tartaric Acid | EtOH:MIBK (1:1) | Filtered |
| 122-3-65 | 0.026 | Tartaric Acid | ACN:Water (98:2) | |
| 122-3-66 | 0.0262 | Toluene Sulfonic Acid | MeOH | thick slurry |
| 122-3-67 | 0.0273 | Toluene Sulfonic Acid | IPA | gum |
| 122-3-68 | 0.0274 | Toluene Sulfonic Acid | EtOH:MeOAc (1:1) | slurry, slight gum |
| 122-3-69 | 0.0264 | Toluene Sulfonic Acid | EtOH:MIBK (1:1) | thick slurry/freezing |
| 122-3-70 | 0.0271 | Toluene Sulfonic Acid | ACN:Water (98:2) | gum like solid upon evaporation |
| 122-3-71 | 0.0255 | Phosphoric Acid | MeOH | slurry |

TABLE 6-continued

Observations after the second re-slurry in process solvent

| Vial # | mass API (g) | Counter ion | Solvent | Observation after 2nd Re-slurry |
|---|---|---|---|---|
| 122-3-72 | 0.0274 | Phosphoric Acid | IPA | |
| 122-3-73 | 0.027 | Phosphoric Acid | EtOH:MeOAc (1:1) | slurry, slight gum |
| 122-3-74 | 0.0252 | Phosphoric Acid | EtOH:MIBK (1:1) | thick slurry |
| 122-3-75 | 0.0261 | Phosphoric Acid | ACN:Water (98:2) | thick slurry |

The experiments that had good/manageable slurry were subjected to PLM analysis. Birefringent solids were observed in two cases, in the case of the experiment L100122-3-20 (fumaric acid), but the XRPD analysis showed it was the counter-ion.

Attempts to Generate Crystalline Salts of SBT-020 with Amino Acids as Counter-Ions Attempts were made with five different amino acids as counter ions (CIs) to generate a crystalline salt with SBT-020. The five different amino acids were L-Lysine, L-Arginine, L-Histidine, L-Aspartic Acid, and L-Tyrosine. The procedure followed was:

1. ~50 mg of SBT-020 Acetate was measured in 2 mL vials.
2. In the case of water soluble AAs (L-Lysine and L-Arginine), 10% solution in water was made and the respective amount that would contain 2.5 Molar Equivalents of CI was added.
3. In the case of other AAs, ~2.5 Molar Equivalents was weighed into the vials initially containing API and 3 V water was added.
4. The slurries/solution was stirred at 50° C. for 30 minutes and the caps were opened to evaporate water over night and were further dried in vacuum oven at 50° C.
5. The respective process solvents were added to the vials and were heated to 45° C. and kept for 2-2.5 hrs, observations were noted down, cooled down to RT.
6. Most of the vials gummed at 45° C., but were brought to slurry through sonication, vortexing and scraping.
7. PLM was performed looking for birefringence, the vials were filtered under the flow of N2, XRPD was performed on wet solids, unique patterns were dried, XRPD was performed on dry solids.

The details of the experiments are provided in Table 7.

Observations of slurry experiments are shown in Table 8.

TABLE 8

Observations from the initial slurries with AAs as CIs

| Vial # | Initial solid/initial slurry at 45° C. | Observations after cooling down |
|---|---|---|
| 122-17-1 | Thick gum on the bottom | Fine slurry with sight gum |
| 122-17-2 | gum on the bottom | thicker slurry |
| 122-17-3 | gum on the bottom | good slurry |
| 122-17-4 | gum on the bottom | slurry, gum on walls and bottom |
| 122-17-5 | gum on the bottom | gumming, no slurry |
| 122-17-6 | gum on the bottom | slurry, gum on walls and bottom |
| 122-17-7 | better solid after drying | slurry, minor gumming |
| 122-17-8 | better solid after drying | slurry |
| 122-17-9 | better solid after drying | good slurry |
| 122-17-10 | better solid after drying | slurry, gum on walls and bottom |
| 122-17-11 | better solid after drying | slurry, gum on walls and bottom |
| 122-17-12 | better solid after drying | good slurry |
| 122-17-13 | Gum on bottom | slurry, gum on walls and bottom |
| 122-17-14 | Gum on bottom | good slurry |
| 122-17-15 | slight gum on bottom | goud slurry |

PLM analysis of all the solids produced showed they were birefringent, however the XRPD analysis of solids produced through the use of the counter-ions L-Histidine, L-Aspartic Acid and L-Tyrosine showed that the solids are CI themselves while the solids produced with the counter-ions L-Lysine in two attempts and that with L-Arginine in EtOH:MIBK (1:1) showed that they are unique.

The experiments L100122-17-1 to L100122-17-6 were repeated for consistency and repeatability (termed L100122-19-1 to L100122-19-6). Similar observations and solids with similar XRPD patterns were observed. However, higher gumming was observed in the case of the experiments

TABLE 7

Initial attempts with Amino Acids as Counter-Ions

| Vial # | mass API (g) | Solvent/Solvent System | Counter ion | CI Molar mass | CI purity | # eq. expected | CI mass expected (g) | µL of CI added | Actual Eq of CI added |
|---|---|---|---|---|---|---|---|---|---|
| 122-17-1 | 0.0448 | MtBE | L-Lysine | 146.19 | 0.98 | 2.5 | 0.0230 | 223 | 2.5 |
| 122-17-2 | 0.0473 | IPA | L-Lysine | 146.19 | 0.98 | 2.5 | 0.0243 | 235 | 2.5 |
| 122-17-3 | 0.0458 | EtOH:MIBK (1:1) | L-Lysine | 146.19 | 0.98 | 2.5 | 0.0235 | 228 | 2.5 |
| 122-17-4 | 0.0448 | MtBE | L-Arginine | 174.2 | 0.98 | 2.5 | 0.0274 | 266 | 2.5 |
| 122-17-5 | 0.0435 | IPA | L-Arginine | 174.2 | 0.98 | 2.5 | 0.0266 | 258 | 2.5 |
| 122-17-6 | 0.0444 | EtOH:MIBK (1:1) | L-Arginine | 174.2 | 0.98 | 2.5 | 0.0272 | 263 | 2.5 |
| 122-17-7 | 0.0472 | MtBE | L-Histidine | 155.15 | 0.99 | 2.5 | 0.0255 | 0.0256 | 2.51 |
| 122-17-8 | 0.0436 | IPA | L-Histidine | 155.15 | 0.99 | 2.5 | 0.0235 | 0.0241 | 2.56 |
| 122-17-9 | 0.0453 | EtOH:MIBK (1:1) | L-Histidine | 155.15 | 0.99 | 2.5 | 0.0244 | 0.0246 | 2.52 |
| 122-17-10 | 0.0446 | MtBE | L-Aspartic Acid | 133.1 | 0.99 | 2.5 | 0.0206 | 0.0214 | 2.59 |
| 122-17-11 | 0.0438 | IPA | L-Aspartic Acid | 133.1 | 0.99 | 2.5 | 0.0203 | 0.0205 | 2.53 |
| 122-17-12 | 0.0434 | EtOH:MIBK (1:1) | L-Aspartic Acid | 133.1 | 0.99 | 2.5 | 0.0201 | 0.0222 | 2.76 |
| 122-17-13 | 0.0444 | MtBE | L-Tyrosine | 181.19 | 0.98 | 2.5 | 0.0283 | 0.0293 | 2.59 |
| 122-17-14 | 0.0434 | IPA | L-Tyrosine | 181.19 | 0.98 | 2.5 | 0.0276 | 0.0281 | 2.54 |
| 122-17-15 | 0.0439 | EtOH:MIBK (1:1) | L-Tyrosine | 181.19 | 0.98 | 2.5 | 0.0279 | 0.0312 | 2.79 |

L100122-19-1 and L100122-19-6, possibly due to higher amount of water left in the solid after drying. The XRPD pattern of L100122-19-6 was similar to that of the solid L100122-17-6.

Scale-Up of the Experiments with L-Lysine and L-Arginine

Two scale-up experiments were performed starting with ~500 mg SBT-020 with 2.5 Equivalents of L-Lysine and L-Arginine, the same procedure that was described earlier was followed, however instead of filtration, the vials were centrifuged, supernatant collected and the pellet was washed with the initial solvent and centrifuged again and the supernatant was collected. This process was repeated two times. These experiments are in progress, the main aim of these experiments was to investigate the stoichiometry through partition of API between the cake and supernatant. The XRDs were consistent with the previous experiments performed with Lysine and Arginine.

The supernatants in both experiments were dried in vacuum oven and were subjected to XRPD and Proton NMR analyses. The XRPD of the dried supernatant from the experiment with L-Lysine (L100122-21-1) showed it is amorphous. The dried solid from the supernatant of the experiment with L-Arginine (L100122-21-2) was also amorphous with traces of the same pattern as the solid in the previous small scale experiment (L100122-17-6). XRPD was also performed on the wet cakes.

Attempts to Produce Co-Crystals of SBT-020 Di-Acetate with L-Lysine and L-Arginine Attempts were made to produce co-crystals of SBT-020 Acetate with L-Lysine and L-Arginine. An API:Co-former ratio of 1:1 was used and these attempts were made through ball-milling. All the solids resulted in amorphous. The details of these experiments are shown in Table 9.

XRPD was performed on the solids that were produced at the end of these attempts and most of them were shown to be amorphous. However, the viscous liquid in the case of the experiment 122-26-1 was dried in vacuum oven and the resulting solid was subjected to XRPD analysis. This solid had a pattern similar to L-Lysine with few extra peaks that belong to the pattern observed earlier. The solid that was produced from the experiment L100122-26-5 was slightly crystalline.

Attempts to Form Salts with Three Other Amino Acids

Three other Amino Acids, L-Proline, L-Threonine, L-Serine were used as CI in an attempt to make salt with SBT-020. All the three amino acids tested were water soluble, hence an initial complete dissolution was achieved with API+2.5 Equivalents CI+ Water. This solution was evaporated and process solvent was added. The procedure followed was the same as the attempts with other amino acids tried earlier (L100122-17-1 to L100122-17-15). The details of these experiments are shown in Table 10.

TABLE 10

Details of experiments with the three additional Amino Acids as CIs

| Vial # (L100-) | mass API (g) | Solvent/Solvent System | Counter ion | CI Molar mass | CI Purity | # eq. expected | CI mass expected (g) | Actual mass of CI added (g) |
|---|---|---|---|---|---|---|---|---|
| 122-26-6 | 0.0381 | IPA | L-Proline | 115.13 | 0.98 | 2.5 | 0.0154 | 0.0154 |
| 122-26-7 | 0.035 | MtBE | L-Proline | 115.13 | 0.98 | 2.5 | 0.0142 | 0.0146 |
| 122-26-8 | 0.0379 | Butanol:DEE (8:2) | L-Proline | 115.13 | 0.98 | 2.5 | 0.0153 | 0.0185 |
| 122-26-9 | 0.038 | IPA | L-Threonine | 119.12 | 0.98 | 2.5 | 0.0159 | 0.0171 |
| 122-26-10 | 0.0357 | MtBE | L-Threonine | 119.12 | 0.98 | 2.5 | 0.0149 | 0.0162 |
| 122-26-11 | 0.0355 | Butanol:DEE (8:2) | L-Threonine | 119.12 | 0.98 | 2.5 | 0.0149 | 0.0160 |
| 122-26-12 | 0.037 | IPA | L-Serine | 105.09 | 0.99 | 2.5 | 0.0135 | 0.0160 |
| 122-26-13 | 0.0342 | MtBE | L-Serine | 105.09 | 0.99 | 2.5 | 0.0125 | 0.0132 |
| 122-26-14 | 0.0361 | Butanol:DEE (8:2) | L-Serine | 105.09 | 0.99 | 2.5 | 0.0132 | 0.0136 |

Observations were made at 45° C. and after 2 days stirring at RT. These observations are shown in Table 11.

TABLE 11

Observation from the experiments with three new amino acids

| Vial # (L100-) | Observation at 45° C. | Observation after stirring at RT for 2 days |
|---|---|---|
| 122-26-6 | Complete dissolution | Cloudy solution with solids |
| 122-26-7 | Slurry, gum on bottom | Slurry |
| 122-26-8 | Complete dissolution | Slurry |
| 122-26-9 | Slurry, slight gum on bottom | Slurry |
| 122-26-10 | Chunky slurry, gum on bottom | Slurry |
| 122-26-11 | Thin slurry | Slurry |

TABLE 9

Details of attempts to produce co-crystals of SBT-020-di-Acetate

| Vial ID (L100-) | Amt of API (mg) | Co-former | co-former (mg) | Solvent | Observation |
|---|---|---|---|---|---|
| 122-26-1 | 23.4 | L-Lysine | 5.0 | IPA (1 V) | Dissolved/viscous liquid |
| 122-26-2 | 24.7 | L-Arginine | 6.1 | EtOH:MIBK (1:1) (1 V) | Gum formation |
| 122-26-3 | 25.5 | L-Lysine | 5.6 | No Solvent | Fine powder |
| 122-26-4 | 25.3 | L-Lysine | 5.5 | IPA (1 V) | Clumping in powder |
| 122-26-5 | 25.6 | L-Arginine | 6.6 | EtOH:MIBK (1:1) (1 V) | Clumping in powder |

TABLE 11-continued

Observation from the experiments with three new amino acids

| Vial # (L100-) | Observation at 45° C. | Observation after stirring at RT for 2 days |
|---|---|---|
| 122-26-12 | Slurry, gum on bottom | Slurry, gum on bottom |
| 122-26-13 | Slurry, minor gum | Slurry |
| 122-26-14 | Thick gel like slurry, gum on bottom | Slurry |

These slurries were subjected to PLM looking for birefringence, all the solids except for 122-26-7 was shown to be birefringent. Also, a small amount was filtered and XRPD analysis was performed. However, XRPD analysis of all the solids revealed that they are CI itself except for the solid L100122-26-14 (from L-Serine) that had additional peaks. L100122-26-14 (Solid with L-Serine as CI made in the solvent Butanol:DEE (8:2)) had additional peaks compared to the CI at 2θ 16.31, 22, 23.51. This solid was subjected to Proton NMR spectroscopy for stoichiometry and DSC was also performed on this solid. The stoichiometry of SBT-020: Serine ~1:21 as determined from Proton NMR.

Attempts to Remove Acetate and Produce a Freebase of SBT-020

Different attempts were made to produce a freebase of SBT-020. The attempts were:

(L100122-24-1) 125 mg of SBT-020 di-Acetate+3 Volumes of Water+44 μL NH$_4$OH, complete dissolution followed by evaporation at 50° C. in vacuum oven—No removal of acetate counter-ion (L100122-24-2) 105 mg SBT 020 di-Acetate+3 Volumes of Water, dissolved and evaporated at 50° C. in vacuum oven—No removal of acetate counter-ion (L100122-27-1) 98.9 mg of SBT 020 di-Acetate+2 mL 1,4 dioxane, dried in Rotavap at 50° C., followed by drying in vacuum oven—No removal of acetate counter-ion (L100122-28-1) 56.4 mg of SBT-020 di-Acetate+3 Vol water, subjected to lyophilization (ongoing)

(L100122-28-2) 59.3 mg of SBT-020 di-Acetate+3 Vol water+1 Vol Glacial Acetic Acid, subjected to lyophiliation (ongoing)

(L100122-28-4) 80.5 mg of SBT-020 di-Acetate+3 V 1 M NaOH, stirring for 30 minutes+12 V DCM, DCM layer extracted and dried in a vacuum ON—proton NMR showed 1 Equivalent of Acetic acid instead of 2 Equivalents, partially successful (L100122-28-5) 41.2 mg of SBT-020 di-Acetate+8 V water+65.2 μL Glacial Acetic Acid, dried in vacuum oven at 55° C.—The equivalents of Acetic Acid did not reduce but peak shifted from 1.85 ppm to 1.93 ppm showing that it was not bound anymore.

Lyophilization of SBT-020 Acetate Dissolved in Water

Two experiments were conducted to test the potential of lyophilization to make the free base of SBT-020. Experiments were conducted with and without the presence of Acetic Acid. None of the experiments showed effective removal of acetate.

Additional Attempts to Make Freebase of SBT-020

Additional attempts to make freebase of SBT-020 were conducted as follow:

L100122-34-1-96 mg of SBT-020-Acetate+192 μL water, dissolved+12.8 mg NaOH in 12.8 μL water. The content was added to 500 μL ACN. The system became a two phase system. Both phases collected and dried. Proton NMR pending on the solids.

L100122-34-2-119 mg of SBT-020 Acetate+238 μL water+22.3 KOH in 22.3 μL water. The content was added to 500 μL ACN. The system resulted in two phases, both of phases dried. Proton NMR pending on the solids.

L100122-34-3—43.1 mg of SBT-020 Acetate+430 μL of saturated potassium carbonate in water added. System gummed, 430 μL of water added, gumming persisted. 200 μL EtOH added, resulted in dissolution. 300 μL water added, system frozen at −20° C. and subjected to lyophilization.

4×~30 mg of solid from L100122-34-3 was slurried in DCM, EtOH, MeOH and IPA. The solid was filtered out and the supernatant dried. Proton-NMR pending.

L100122-34-4—55.9 mg of SBT-020 Acetate+560 μL of saturated sodium carbonate added. System gummed, 560 μL of water added, gumming persisted. 200 μL EtOH added, resulted in dissolution. 100 μL water added, system frozen at −20° C. and subjected to lyophilization.

4×~30 mg of solid from L100122-34-3 was slurried in DCM, EtOH, MeOH and IPA. The solid was filtered out and the supernatant dried. Proton-NMR performed on the solid from DCM (L100122-36-4). This did not extract the freebase, Solid from MeOH showed corresponding peak of Acetate (L100122-36-6), possibly due to high solubility of sodium acetate in MeOH. Experiment with IPA pending.

L100122-35-1—24.1 mg Chloride of SBT-020 was dissolved in 6 V water and 51.5 mg Dowex 1×8 Chloride form resin was added. The vial was stirred at RT for ~2 hours. The vial was filtered and dried in vacuum oven at RT. The solid was subjected to proton NMR—did not show significant presence of Acetate, comparison with HCl salt pending.

The pH of the solid obtained from the experiment L100122-35-1 (Dowex resin treatment of HCl salt) in 1:1 Water:MeOH was measured with a pH paper and was found to be ~5.5. This was a clear indication that this solid was still the salt of SBT-020 rather than its FB as FB formation generally results in an increase in the pH of the solution.

Slurry of the solids produced through the treatment of SBT-020 Acetate with Carbonates of Na and K The solids that were produced after the lyophilization of SBT-020 Acetate solution treated with Na$_2$CO$_3$ (L100122-34-4) and K$_2$CO$_3$ (L100122-34-3) were slurried in IPA and the supernatants were separated, dried and were subjected to proton NMR analyses. Both the experiments did show substantial amount of Acetate.

Attempts to Produce FB of SBT-020 with 50% NaOH and KOH Solutions

Attempts were made to produce FB of SBT-020 by dissolving SBT-020 acetate in 50% (W/W) Aq. solutions of NaOH and KOH.

L100122-38-1—4V of 50% (W/W) Aq. Solution of NaOH was added to ~50 mg of SBT-020 Acetate. This resulted in severe gumming 4V of water was added, partial dissolution achieved, however gumming persisted. The gum and supernatant were separated, dried in vacuum oven and were subjected to proton NMR—solid from gum had 1.86 M equivalents of Acetate and the supernatant did not show any API.

L100122-38-2—4V of 50% (W/W) Aq. Solution of KOH was added to ~50 mg of SBT-020 Acetate. This resulted in severe gumming 4V of water was added, partial dissolution achieved, however gum persisted. The gum and supernatant were separated, dried in vacuum oven and were subjected to proton NMR—solid from gum had 1.3 M equiv. of Acetate and the supernatant did not show any API.

~10-15 mg of these solids were further slurried in solvents DCM:TFE (1:1) and MeTHF to extract the FB if formed. However, the yield was extremely low in all cases (<10%).

Attempts to Produce FB of SBT-020 in Less Concentrated KOH Solution

As the use of KOH was partially successful in compared with NaOH in the case of the experiments L100122-38-1 and L100122-38-2, another attempt was made by treatment with 5 M equiv. of KOH (L100122-40-1). ~119.3 mg of SBT-020 Acetate was dissolved in 5V water and 46.1 µL of 50% (W/W) KOH solution (5 M Eq) was added. The system resulted in emulsion. 2V of water added, emulsion persisted. The vial was centrifuged and the phases were separated. The phase that was apparently organic was dried and subjected to proton NMR—showed only ~0.3 M Equivalents of Acetate. Additional attempts with different amounts of KOH were performed. SBT-020 Acetate was first dissolved in 4 V water and KOH solution was added (Table 12).

TABLE 12

Additional attempts to treat SBT-020 Acetate with different concentrations of KOH

| Exp ID (L100-) | Amt (mg) | Eq of KOH | Comment |
| --- | --- | --- | --- |
| 122-40-2 | 92.1 | 2.1 | Dissolved |
| 122-40-3 | 96.9 | 4 | Dissolved |
| 122-40-4 | 93.3 | 6 | Emulsion |

Additional amount of KOH solution was added to vials L100122-40-2 and L100122-40-3 to make the total concentration of KOH to be 7 and 9 Equivalents. Both these additions resulted in an emulsion. The phases were separated and dried all the three vials. The apparent organic phase in all the three cases that was dried was subjected to proton NMR analyses—all the three solids showed to retain 0.4-0.5 M equivalents of acetate counter-ion.

Exposure of all Amorphous Salts to Humidity

Although amorphous, salts that were produced earlier were exposed to Humidity through saturated NaCl solution (75% RH at room temperature) for stability assessment. Out of all salts exposed, Tosylate and Phosphate demonstrated physical stability upon humidity exposure. The details of the experiments are shown in Table 13.

TABLE 13

Details of experiments performed by exposing salts produced during initial screening to humidity

| Vial ID | CI | Observation after 2 days exposure in humidity |
| --- | --- | --- |
| SBT-020 di-Acetate | Acetic acid | Deliquesced |
| L100122-3-2 | Benzene Sulfonic Acid | Deliquesced |
| L100122-3-3 | Benzene Sulfonic Acid | Deliquesced |
| L100122-3-5 | Benzene Sulfonic Acid | Deliquesced |
| L100122-3-6 | Benzoic Acid | Deliquesced |
| L100122-3-8 | Benzoic Acid | Deliquesced |
| L100122-3-10 | Benzoic Acid | Deliquesced |
| L100122-3-11 | Citric Acid | Deliquesced |
| L100122-3-15 | Citric Acid | Deliquesced |

TABLE 13-continued

Details of experiments performed by exposing salts produced during initial screening to humidity

| Vial ID | CI | Observation after 2 days exposure in humidity |
| --- | --- | --- |
| L100122-3-16 | Fumaric Acid | Deliquesced |
| L100122-3-19 | Fumaric Acid | Deliquesced |
| L100122-3-22 | Hydrobromic Acid | Deliquesced |
| L100122-3-23 | Hydrobromic Acid | Deliquesced |
| L100122-3-26 | Hydrochloric Acid | Deliquesced |
| L100122-3-29 | Hydrochloric Acid | Deliquesced |
| L100122-3-33 | Malic Acid | Deliquesced |
| L100122-3-34 | Malic Acid | Deliquesced |
| L100122-3-41 | Methane Sulfonic Acid | Deliquesced |
| L100122-3-54 | Sulfuric Acid | Deliquesced |
| L100122-3-67 | Toluene Sulfonic Acid | Good solid, very slight clumping |
| L100122-3-68 | Toluene Sulfonic Acid | Good solid, very slight clumping |
| L100122-3-71 | Phosphoric Acid | Good solid, very slight clumping |

Among all the salts exposed to humidity, the tosylate tended to have the best stability under humidity exposure. Qualitative solubility in water was measured to be more than 100 mg/mL at RT. Proton NMR also showed API:CI ratio of 1:2 which was expected as this material was generated through solvent evaporation. No signs of acetic acid were observed. DSC was also performed on this solid which showed a small melting onset of 138° C. PLM of this solid showed some birefringence and also the XRPD analysis showed it was slightly crystalline.

Exposure of Other Salts to Moisture

Other salts of SBT-020 that were made during the initial screening that were missing in Table 13 were exposed to 75% RH. The missing salts were Maleate, Salicylate, Tartarate (repeat), Succinate and Phosphate (repeat). Tartarate and Phosphate became wet, though they did not deliquesce even after a week of exposure to Humidity.

Additional Proton-NMR Analyses

Due to the success of the Tosylate formation of SBT-020 in completely removing Acetic Acid/Acetate, selected versions of the Sulfate and Tatrate of SBT-020 were subjected to proton-NMR analysis to test if the pKa of the Counter Ion has an effect in removing the Acetic Acid/bound Acetate to SBT-020. Sulfate removed Acetate/Acetic Acid much effectively compared to Tartrate. This was a clear indication that the pKa of the CI has a profound impact in removing Acetic Acid/bound Acetate.

Preparation of Salts of SBT-020 with Excess Counter Ions

Chloride, Bromide, Methane Sulfonate, Benzene Sulfonate, Tartrate and Phosphate salts of SBT-020 were made from the Acetate of SBT-020 and with 6 equiv. of CI instead in an attempt to make salts that are free of Acetate/Acetic Acid. Acetate of SBT-020 was initially dissolved in MeOH and the respective CI was added. The vials were stirred at 50° C. and were evaporated. Methane Sulfonate and Benzene Sulfonate resulted in a gum that did not turn into solid even after extended drying in vacuum oven. The rest of the experiments produced solid, that was stirred in MIBK, filtered and subjected to proton NMR. Again, the formation of the Chloride and Bromide of SBT-020 completely removed Acetate/Acetic acid, while Tartrate and Phosphate salts retained 1.16 M equiv. and 0.53 M equiv. of Acetate/Acetic Acid. The details of these experiments are shown in Table 14.

TABLE 14

Details of the salt formation experiments performed with 6 equiv. CI

| Exp ID (L100-) | Salt | Amount of SBT-020 Acetate (mg) | Condition after evaporation |
|---|---|---|---|
| 122-53-1 | Chloride | 100.0 | Solid |
| 122-53-2 | Bromide | 100.5 | Solid |
| 122-53-3 | Methane Sulfonate | 104.2 | Gum |
| 122-53-4 | Benzene Sulfonate | 104.2 | Gum |
| 122-53-5 | Tartrate | 101.2 | Solid |
| 122-53-6 | Phosphate | 99.1 | Solid |

Various Salts of SBT-020—Repeats in a Non-Aqueous System

Various salts of SBT-020 were attempted to be made with different counter-ions in IPA. These experiments were started with ~75-80 mg of the di-Acetate of SBT-020. 3 equivalents of the CI was added to each of the respective vials (in the case of solid CIs, in the case of CI that are solutions, they are added after solvent addition). The vials were heated to 45° C. and were kept at 45° C. for 90 minutes. The vials were cooled to RT naturally and were left stirring O/N. Gumming was broken down periodically to produce good slurries. The details and observations from the experiments is shown in Table 15. The observations from these salt formation experiments is also shown in Table 16.

TABLE 15

Details of various salt formation experiments performed in IPA

| Vial # | amt of diacetate (g) | Solvent | CI | CI MW | CI purity | # eq. expected | CI mass expected (g) | Actual mass added (g) | Eq of CI added |
|---|---|---|---|---|---|---|---|---|---|
| 125-10-2 | 0.077 | IPA | Benzenesulfonic Acid | 158.17 | 0.98 | 3 | 0.0513 | 0.0519 | 3.03 |
| 125-10-3 | 0.0722 | IPA | Benzoic Acid | 122.12 | 0.995 | 3 | 0.0366 | 0.0381 | 3.12 |
| 125-10-4 | 0.0743 | IPA | Citric Acid | 192.124 | 0.995 | 3 | 0.0593 | 0.0621 | 3.14 |
| 125-10-5 | 0.0739 | IPA | Fumaric Acid | 116.07 | 0.99 | 3 | 0.0358 | 0.0389 | 3.26 |
| 125-10-6 | 0.0732 | IPA | Hydrobromic Acid | 80.91 | 0.48 | 3 | 0.0510 | 342.0 | 3.00 |
| 125-10-7 | 0.0748 | IPA | Hydrochloric Acid | 36.46094 | 0.365 | 3 | 0.0309 | 617.9 | 3.00 |
| 125-10-8 | 0.0702 | IPA | Malic Acid | 134.0874 | 1 | 3 | 0.0389 | 0.0389 | 3.00 |
| 125-10-9 | 0.0718 | IPA | Methanesulfonic Acid | 96.1 | 0.98 | 3 | 0.0291 | 196.3 | 3.00 |
| 125-10-10 | 0.0712 | IPA | Salicylic Acid | 138.121 | 0.99 | 3 | 0.0410 | 0.0514 | 3.76 |
| 125-10-11 | 0.0748 | IPA | Sulfuric Acid | 98.079 | 0.95 | 3 | 0.0319 | 173.3 | 3.00 |
| 125-10-12 | 0.0736 | IPA | Succinic Acid | 118.09 | 0.99 | 3 | 0.0363 | 0.0397 | 3.28 |
| 125-10-13 | 0.0763 | IPA | Tartaric Acid | 150.087 | 0.999 | 3 | 0.0473 | 0.0486 | 3.08 |
| 125-10-14 | 0.0713 | IPA | Maleic Acid | 116.07 | 0.99 | 3 | 0.0345 | 0.0379 | 3.29 |
| 125-10-15 | 0.0758 | IPA | Nitric Acid | 63.01 | 0.68 | 3 | 0.0290 | 205.3 | 3.00 |
| 125-10-16 | 0.0676 | IPA | Phosphoric Acid | 98 | 0.98 | 3 | 0.0279 | 169.2 | 3.00 |

TABLE 16

Observations after the vials were cooled to RT. Heptane was added to the vials that were gummed in an attempt to make manageable slurries that can be filtered.

| Exp ID | CI | Observation at RT | Heptane addition (µL) |
|---|---|---|---|
| 125-10-2 | Benzenesulfonic acid | Gum | 100 |
| 125-10-3 | Benzoic acid | Clear solution | 100 |
| 125-10-4 | Citric acid | slurry | — |
| 125-10-5 | Fumaric acid | slurry | — |
| 125-10-6 | Hydrobromic acid | gum | 80 |
| 125-10-7 | Hydrochloric acid | slurry | — |
| 125-10-8 | Malic acid | slurry | — |
| 125-10-9 | Methanesulfonic acid | Gum | 60 |
| 125-10-10 | Salicylic acid | Clear solution | 100 |
| 125-10-11 | Sulfuric acid | slurry | — |
| 125-10-12 | Succinic acid | Gum on the bottom, broken down | — |
| 125-10-13 | Tartaric acid | slurry | — |
| 125-10-14 | Maleic Acid | Thin slurry, gum on the bottom | 60 |
| 125-10-15 | Nitric Acid | Gum on the bottom, broken down | 60 |
| 125-10-16 | Phosphoric Acid | slurry | — |

The experiments 125-10-2, 10-3, 10-6, 10-10 and 10-14 did not produce manageable slurries even after the addition of Heptane. These vials were evaporated at RT, further dried in a vacuum oven at RT and were re-slurried in MeOAc. Good slurries were observed in the case of experiments 125-10-2 (Benzene sulfonic acid) and 125-10-6 (HBr) while gumming persisted in other cases. 125-10-14 (Maleic Acid) was centrifuged to separate supernatant. While the vial 125-10-10 (Salicylic acid) was dried in a vacuum oven at 50° C. XRPD was performed on all the salts that were filtered and were amorphous. H-NMR was performed for stoichiometry. TGA/DSC analyses was also performed on all the salts obtained. All the salts exhibited a very broad melting peaks followed by decomposition with no defined/sharp melting regions which is also a tendency of amorphous solids. The salt formation experiments with the CIs Fumaric Acid, Malic Acid and Succinic Acid was re-performed due to unavailability of the material for TGA/DSC analysis after performing XRPD and H-NMR. The same procedure as described earlier was followed for these repeats. The details and observations from these experiments is provided in Table 17. All the three solids were amorphous upon filtration.

TABLE 17

Repeats of experiments with Fumaric Acid, Malic Acid and Succinic Acid

| Exp ID | Amt of di-Acetate(g) | CI | Amt of CI (g) | Eq of CI | Observation at 45° C. | Observation at RT |
|---|---|---|---|---|---|---|
| 125-17-1 | 0.0741 | Fumaric Acid | 0.0397 | 3.32 | Minor gumming | Dry gum, broken down to slurry |
| 125-17-2 | 0.0752 | Malic Acid | 0.0464 | 3.34 | Minor gumming | Gum broken down to slurry |
| 125-17-3 | 0.073 | Succinic Acid | 0.0381 | 3.18 | Minor gumming | Thicker gum, broken down to slurry |

Evaporation Tests to Determine the Effect of Dissolution in Water Followed by Evaporation with Weak CIs Salt formation was attempted by dissolving the di-Acetate of SBT-020 along with the respective CI in water. The dissolved solution was stirred at 50° C. for about 1 hour and the whole clear solution was evaporated to form a gel. These gels were further dried in a vacuum oven at 50° C. The resultant solids were re-slurried in MIBK to remove any unevaporated Acetic Acid present in the system that was formed due to salt formation. The slurries were filtered and were dried to recover the respective salt. However, HPLC analysis of the solids obtained in the case of stronger CIs such as Chloride, Sulfate etc., showed the presence of an additional peak which was suspected to be a result of possible hydrolysis of SBT-020 during evaporation in water in the presence of these strong CIs. Tests were performed by dissolving the di-Acetate of SBT-020 along with 3 equivalents of weaker acids in 10 V water. The solutions were stirred at 50° C. for 2 hours and were evaporated on hot plates at 50° C. until a thick gel was formed. These gels were further evaporated in a vacuum oven at 50° C. to make solids. HPLC was performed on these solids. The details of these experiments are provided in Table 18.

TABLE 18

Details of water evaporation experiments performed with weaker CIs

| Exp ID | di-Acetate (mg) | CI | CI (mg) |
|---|---|---|---|
| 125-17-4 | 44.9 | L-Lysine | 26.8 |
| 125-17-5 | 48.2 | L-Arginine | 31.5 |
| 125-17-6 | 45.5 | Tartratic Acid | 32.1 |
| 125-17-7 | 45.6 | Succinic Acid | 23.3 |
| 125-17-8 | 45.5 | Citric Acid | 35.8 |

HPLC analysis of the solids showed no presence of the second peak that was suspected to be a result of hydrolysis as in the case of solids produced with stronger CIs.

Polymorph Screening on the Tosylate of SBT-020

Tosylate of SBT-020 was initially prepared by dissolving di-Acetate of SBT-020 and 3 M Equivalents of Toluene sulfonic acid monohydrate in 3 V Water, followed by evaporation. The Tosylate of SBT-020 thus formed was re-slurried in MIBK to remove any unevaporated acetic acid that was formed as a result of the salt formation with Toluene sulfonic acid. However, HPLC analysis of this Tosylate of SBT-020 showed the presence of another peak other than the FB which was possibly formed due to hydrolysis of the FB.

Preparation of the Tosylate of SBT-020 in EtOH System

Alternatively, the Tosylate of SBT-020 was prepared by dissolving the di-acetate of SBT-020 along with 3 equiv. of Toluene sulfonic acid monohydrate in EtOH (Exp Id: L100122-89-1). The clear solution quickly resulted in an unstirrable slurry within a span of 1 hour. The system was left at RT O/N and the whole unstirrable slurry was evaporated at RT in a vacuum oven. The solid was subjected to HPLC analyses and the second peak that was assumed to be formed due to possible hydrolysis was not seen. This solid was also subjected to H-NMR and an API:CI ratio of 1:3.25. 0.4 equiv. of free acetic acid were also seen in the spectrum. Due to the success in making cleaner Tosylate of SBT-020 in EtOH, additional Tosylate of SBT-020 was prepared starting with about 2 g of di-Acetate of SBT-020 (Exp Id: L100122-90-1).

Slurry Experiments

Slurry experiments of Tosylate were re-performed with the new batch of Tosylate made in EtOH. These slurry experiments are performed at two different temperatures RT and 45° C. ~30 mg of Tosylate was slurried in 400 μL solvent. All the slurries were performed for 5 days before being subjected to XRPD analyses. The details and observations from these slurry experiments are provided in Table 19 and Table 20.

TABLE 19

Details and observations from the slurry experiments on the Tosylate of SBT-020 performed at RT

| Exp ID | Solvent | Observation |
|---|---|---|
| 122-91-1 | MeOH | Clean solution |
| 122-91-2 | Abs. EtOH | Unstirrable slurry |
| 122-91-3 | MtBE | Slurry |
| 122-91-4 | MeOAc | Slurry |
| 122-91-5 | Heptane | Slurry |
| 122-91-6 | MIBK | Slurry |
| 122-91-7 | EtOAc | Slurry |
| 122-91-8 | IPA | Slurry |
| 122-91-9 | CAN | slurry/minor gum formation |
| 122-91-10 | THF | gum |
| 122-91-11 | Toluene | slurry |
| 122-91-12 | Acetone:Water (98:2) | slurry |
| 122-91-13 | DMAc:MeOAc (1:9) | Clear solution, additional Tosylate added |
| 122-91-14 | DCM | Evap |
| 122-91-15 | IPA:Water (98:2) | Unstirrable slurry |
| 122-91-16 | Butanol | Unstirrable slurry |
| 122-91-17 | BA | Clear solution, additional Tosylate added |

TABLE 20

Details and observations from slurry experiments with the Tosyalte of SBT-020 performed at 45° C.

| Exp ID | Solvent | Observation |
|---|---|---|
| 122-91-18 | MeOH | Clean solution |
| 122-91-19 | Abs. EtOH | Unstirrable slurry |
| 122-91-20 | MtBE | Slurry |
| 122-91-21 | MeOAc | gum |
| 122-91-22 | Heptane | Slurry |

TABLE 20-continued

Details and observations from slurry experiments with the Tosyalte of SBT-020 performed at 45° C.

| Exp ID | Solvent | Observation |
|---|---|---|
| 122-91-23 | MIBK | Slurry |
| 122-91-24 | EtOAc | Slurry/minor gumming |
| 122-91-25 | IPA | very thick/unstirrable slurry |
| 122-91-26 | CAN | gum |
| 122-91-27 | THF | gum |
| 122-91-28 | Toluene | Thick slurry |
| 122-91-29 | Acetone:Water (98:2) | gum |
| 122-91-30 | DMAc:MeOAc (1:9) | Clear solution, additional Tosylate added |
| 122-91-31 | IPA:Water (98:2) | Unstirrable slurry |
| 122-91-32 | Butanol | Unstirrable slurry |
| 122-91-33 | BA | Clear solution, additional Tosylate added system oiled |

XRPD was performed on the available solids obtained from high temperature slurry experiments at 45° C. on the Tosylate of SBT-020. The solids from experiments L100122-91-31, 91-32 and 91-25 were performed after about 5 days of slurry at 45° C. while all the other XRPDs were performed after about a week after slurrying at 45° C. If the system was a slurry, a small amount was filtered and was subjected to XRPD immediately. In the case of unstirrable slurries, a small amount of the whole system was applied on a zero-background plate and was subjected to XRPD analysis. The solids from the slurries in MtBE (L100122-91-20), Heptane (L100122-91-22), MIBK (L100122-91-23) and Toluene (L100122-91-28) showed very faint signs of crystallinity while the slurry in IPA:Water (98:2) (L100122-91-31) showed highest crystallinity among all the experiments performed so-far. However, this solid lost its crystallinity upon drying. The unstirrable slurries in EtOH (L100122-91-19), IPA (L100122-91-25) and Butanol (L100122-91-32) also displayed some crystallinity.

An attempt was made to obtain a higher resolution XRPD pattern of the Tosylate of SBT-020 in the case of the experiment L100122-91-31 (HT slurry in IPA:Water (98:2)) through exposing the solid to x-rays for a longer time at each '2θ' interval. This run was about 30 minutes compared to the other pattern that was captured in 5 minutes. A transformation/reduction in crystallinity was observed even within the 30 minutes of exposure. A substantial decrease in the crystallinity and also a transformation in the pattern was observed during the longer run.

Repeats of Experiments that Resulted in Weakly Crystalline Forms of the Tosylate Cooling crystallization and anti-solvent crystallization experiments that resulted in weakly crystalline forms of the Tosylate were repeated with the Tosylate that was made in EtOH. The details of these experiments are provided in Table 21 and Table 22.

TABLE 21

Details of anti-solvent crystallization experiments performed with the Tosylate prepared in EtOH

| Exp ID | Amt of Tosylate (mg) | Anti-Solvent | Amt of Anti-solvent (V) | Comment |
|---|---|---|---|---|
| 122-92-2 | 147 | MIBK | 2 | Dissolved in 3 V MeOH, Anti-solvent added over 30 minutes, haziness was observed. Seeded with 122-81-7, unstirrable slurry |
| 122-92-3 | 144 | MEK | 2.5 | Dissolved in 3 V MeOH, Anti-solvent added over 30 minutes, haziness was observed. Seeded with 122-81-7, unstirrable slurry |

TABLE 22

Cooling crystallization experiments with the Tosylate prepared in EtOH

| Exp Id | Amt of Tosylate | Solvent | Amt (V) | Comment |
|---|---|---|---|---|
| 122-92-4 | 102.7 | EtOH | 36 | Complete dissolution did not occur, unstirrable slurry formation was observed around 7.5 V of EtOH addition. System filtered at the end |
| 122-92-5 | 108.3 | IPA:MeOH | 6 V IPA + 6 V MeOH | Complete dissolution, system cooled down to RT and unstirrable slurry formation observed. 2 V of 1:1 IPA:MeOH added and the system filtered |
| 122-92-6 | 109.2 | EtOH:MeOH (9:1) | 15.5 | 2 additional volumes of Straight MeOH were added for dissolution. System cooled to RT naturally, unstirrable slurry formation was observed |

All the solids resulted in weakly crystalline XRPD patterns. All of the unstirrable slurries were dried in a vacuum oven at RT. All the vials were dried at RT to minimize exposure to heat. The vials L100122-92-4 and L100122-92-5 resulted in a clean solid, however, slight discoloration/browning was observed in the case of the experiments L100122-92-2 and 92-3. Relatively this browning was more profound in the case of the experiment L00122-92-3 (Anti-solvent crystallization in MeOH/MEK system). The dry solids were also subjected to XRPD analysis. XRPD analysis showed a profound reduction in the crystallinity of the solids. TGA/DSC analysis were also performed on these dry solids.

HPLC analyses was also performed on the four solids obtained through anti-solvent and cooling crystallization to assess the stability of the Tosylate at these conditions and also to assess the impurity rejection through these treatments. The di-acetate of SBT-020 (L100122-74-9) and also the initial Tosylate made in EtOH that is used for these experiments (L100122-90-1) was also provided for reference. The Tosylate that is produced through cooling/slurry in EtOH (L100122-92-4) proved to me the most cleaner in terms of impurity rejection. All the other Tosylates that are produced in MeOH solvent systems resulted in the generation of an impurity at an RRT 1.33. A small part of solid from the discolored part of L100122-92-3 was also subjected to HPLC analysis. This solid showed the presence of several impurities.

Slurry Experiments in EtOH:Water Systems

Two experiments were performed by slurrying the Tosylate in EtOH with 1% and 2% water V/V in an attempt to improve its crystallinity. Both of the experiments resulted in amorphous solids that showed very weak signs of crystallinity. The details of these experiments is provided in Table 23.

TABLE 23

Details of slurry experiments in EtOH:Water system

| Exp Id | Amt of Tosylate | Solvent | Amt (V) | Comment |
|---|---|---|---|---|
| 122-92-8 | 68.8 | EtOH:Water (98:2) | 10 | Slurried at RT O/N, Thick/unstirrable slurry |
| 122-92-9 | 65.3 | EtOH:Water (99:1) | 10 | Slurried at RT O/N, Think/unstirrable slurry |

Cooling Crystallization in MeOH:MIBK and MeOH:MEK Solvent Systems

Tosylate is dissolved in MeOH:MIBK and MeOH:MEK (1:1 vol) solvent systems at 50° C. and were slowly cooled to RT over a span of 3 hours. The details of these experiments is provided in Table 24.

TABLE 24

Cooling crystallization in MeOH:MIBK and MeOH:MEK solvent systems

| Exp Id | Amt of Tosylate (mg) | Solvent | Amt (V) | Comment |
|---|---|---|---|---|
| 125-1-1 | 74.5 | MeOH:MIBK (1:1) | 3 | Dissolved, resulted in unstirrable slurry around 40° C. |
| 125-1-2 | 74.4 | MeOH:MEK (1:1) | 3 | Dissolved, no solid formation, seeded at RT, resulted in solid formation |
| 125-1-3 | 33.7 | MeOH:MIBK (1:1) | 2.4 | Unstirrable slurry at 50° C. upon addition of around 2 V solvent |
| 125-1-4 | 37.4 | MeOH:MEK (1:1) | 1.5 | Dissolved, no solid formation, seeded at RT, resulted in solid formation |

Follow-Up Experiments with IPA, Butanol and MeOH Solvent Systems Temperature Cycling/Cooling Crystallization Experiments Due to the success with IPA:Water solvent systems, additional cooling/temperature cycling crystallization experiments were performed with IPA, Butanol paired with water and BA. Experiments were also performed with MeOH:MIBK and MeOH:MEK ratios to see if these solvent systems result in crystalline solids. ~55-60 mg of the Tosylate of SBT-020 that is prepared in EtOH followed by drying was weighed in 2 mL vials and the respective solvent was added. The vials were stirred at RT for ~10 minutes and were heated to 45° C. in 30 minutes. The vials were kept at 45° C. for 30 minutes and were cooled down to RT slowly in 5 hours. Observations were noted down at 45° C. and at 34° C. The details of these experiments and the observations were shown in Table 25.

TABLE 25

Details of cooling/temperature cycling experiments with various solvent systems

| Exp ID | Amt (mg) | Solvent system | Initial volumes | Observation at 45 C. | Observation at 34 C. |
|---|---|---|---|---|---|
| 125-4-1 | 54.9 | IPA:Water (99:1) | 7 | Slurry, gelling | thick slurry |
| 125-4-2 | 58.2 | IPA:Water (98:2) | 7 | thick slurry, gelling | unstirrable slurry |
| 125-4-3 | 53.6 | IPA:Water (95:5) | 7 | Clear solution | unstirrable slurry, paste like |
| 125-4-4 | 55.1 | MEK:MeOH (1:1) | 4 | Clear solution | Clear solution |
| 125-4-5 | 53.6 | MEK:MeOH (7:3) | 7 | unstirrable slurry | unstirrable slurry |
| 125-4-6 | 58.2 | MIBK:MeOH (1:1) | 4 | thick slurry, gelling | unstirrable slurry |
| 125-4-7 | 57.5 | MIBK:MeOH (7:3) | 7 | unstirrable slurry | unstirrable slurry |
| 125-4-8 | 59.3 | IPA:BA (95:5) | 7 | slurry | thick slurry |
| 125-4-9 | 56.8 | IPA:BA (98:2) | 7 | Slurry, gelling | Slurry, gelling |
| 125-4-10 | 58.8 | Butanol:Water (95:5) | 7 | Clear solution | Clear solution |
| 125-4-11 | 56.8 | Butanol:Water (98:2) | 7 | unstirrable slurry | unstirrable slurry |

The vial L100125-4-3 that resulted in unstirrable slurry was heated up to 45° C. and a very thin slurry formation was observed. This vial was transferred to a hot plate at 35° C. and was left at this temperature O/N. Thick paste-like slurry was observed when the vial was kept at 35° C. O/N. XRPD was performed on all samples that had solids. Highest crystallinity was shown in IPA:Water (95:5 Vol) where dissolution followed by crystallization occurred upon cooling the system from 45° C. Good crystallinity was also exhibited by the slurry in MIBK:MeOH (1:1). Weakly crystalline pattern was also observed in the case of solid slurried in a Butanol:Water system.

The vials with IPA:BA solvent systems became a thick paste like slurries upon leaving them at RT O/N while all the other vials became unstirrable slurries that are a single piece, while the vial with the solvent system Butanol:Water (95:5 Vol) remained a clear solution. Cyclohexane was added to this vial in aliquots of 25 µL and was left stirring at RT after solids were observed.

The vials that resulted in unstirrable slurries were heated to 45° C. and the same solvent was added in aliquots of 25 µL initially, followed by 100 µL additions until manageable slurries were observed. Around 25-30 volumes of solvent had to be added in order to obtain a manageable slurry. All the manageable slurries were first cooled down to 35° C. and were further cooled down to RT and were left at RT for 10 days. All the vials were manageable slurries. The details of these additions were shown in Table 26. A small sample was drawn from each vial and XRPD was performed after leaving the slurries at RT for 10 days.

No observable change in the XRPD patterns were observed after 10 days slurry at RT.

TABLE 26

Details of additions performed to make manageable slurries

| Exp ID (L100-) | Amt (mg) | Solvent system | Total additional solvent | Volumes | Comment |
|---|---|---|---|---|---|
| 125-4-1 | 54.9 | IPA:Water (98:1) | 1825 | 33.2 | Transferred to a 4 mL vial |
| 125-4-2 | 58.2 | IPA:Water (98:2) | 1825 | 31.4 | Transferred to a 4 mL vial |
| 125-4-3 | 53.5 | IPA:Water (95:5) | — | — | Very thin slurry cooled to 35° C. |
| 125-4-4 | 55.1 | MEK:MeOH (1:1) | — | — | Clear solution cooled to 35° C. |
| 125-4-5 | 53.5 | MEK:MeOH (7:3) | 925 | 17.3 | Manageable slurry |
| 125-4-6 | 58.2 | MIBK:MeOH (1:1) | 350 | 6.0 | Manageable slurry |
| 125-4-7 | 57.5 | MIBK:MeOH (7:3) | 1625 | 28.3 | Transferred to a 4 mL vial |
| 125-4-8 | 59.3 | IPA:BA (95:5) | 2025 | 34.1 | Transferred to a 4 mL vial |
| 125-4-9 | 56.8 | IPA:BA (98:2) | 1625 | 28.6 | Transferred to a 4 mL vial |
| 125-4-10 | 58.8 | Butanol:Water (95:5) | | | 225 µL of Hepune added |
| 125-4-11 | 56.8 | Butanol:Water (98:2) | 900 | 15.8 | Manageable slurry |

Heptane was added to the slurry in IPA:Water (99:1 Vol) in aliquots of 25 µL. A total of 625 µL is added. However, a slight but not substantial improvement in rheology was observed.

Crystallization Followed by Dissolution in IPA:Water System

Two experiments were performed by initially dissolving the Tosylate of SBT-020 in IPA:Water system. Replica experiments were performed in 2 and 4 mL vials to test the effect of stirring on rheology of the system and also to see if there is a difference in terms of heat transfer. The details of these experiments is provided in Table 27.

TABLE 27

Details of dissolution followed by crystallization experiments with IPA:Water solvent systems

| Exp ID (L100-) | Amt (mg) | IPA (V) | Water (µL) | Comment | Observation at 50° C. | Observation at 42° C. |
|---|---|---|---|---|---|---|
| 125-7-1 | 76.1 | 10 | 40 | 2 mL vial with 5 mm stir bar. Heated to 60° C., IPA added, Water added X 10 µL, gummed, broken down | Flowable slurry | Unstirrable slurry |
| 125-7-2 | 76 | 10 | 40 | 4 mL vial with 10 mm stir bar. Heated to 60° C., IPA added, Water added X 10 µL, no gumming observed | Flowable slurry | Unstirrable slurry |

Both the experiments resulted in complete dissolution after the addition of 40 µL Water (~0.53 V) at 60° C. Post dissolution, Both vials were cooled down to 55° C. and seeding was performed with slurry from L100125-4-3 (Cooling/temperature cycling experiment in IPA:Water (95:5 Vol). The vials were heated back up to 57° C., seed retained.

and IPA:Water solvent systems to identify the most fruitful solvent system in terms of rheology and perform a scale-up with the selected solvent system. The details of these experiments performed with IPA:MeOH solvent system were provided in Table 28. All the vials were heated to 60° C. after the addition of IPA and MeOH was added at this temperature for dissolution. After dissolution, the vials were cooled down to 50-55° C. and seeding was performed with L100125-7-2.

TABLE 28

Details of salt formation followed by cooling crystallization experiments performed with IPA:MeOH solvent systems

| Exp ID (L100-) | Amt of di-Acetate (mg) | Amt of p-TSA monohydrate (mg) | IPA (V) | MeOH (µL) | Comment | Obsevation at 52° C. |
|---|---|---|---|---|---|---|
| 125-9-1 | 89.3 | 74.6 | 8 | 240 | Almost clear solution obtained with 40 µL MeOH addition, 20 µL additional MeOH resulted in Oiling (?), continued addition for dissolution | Cloudy |
| 125-9-2 | 90.5 | 74.5 | 15 | 380 | Gumming with 80 µL MeOH, dissolved upon further addition | Slightly Cloudy |
| 125-9-3 | 82.3 | 69.8 | 8 | 40 | | Cloudy |
| 125-9-4 | 84 | 69.8 | 15 | 200 | Gumming with 80 µL MeOH, dissolved upon further addition | Clear solution |

Both vials were cooled down to 45-50° C. and both the vials precipitated as thick slurries at 47° C.

The vials were then heated to 50° C. and flowable slurry formation was observed. Both the vials are then cooled down to 44° C. over a span of 45 minutes. The vials were left for about 90 minutes and very thick non-flowable slurry formation was observed.

Heptane was added to both the vials to make the system in 1 V additions (76 µL). 4 V of Heptane was added The vials were kept at 52° C. at 10 minutes and unstirrable slurry formation was observed in all the four cases. 200 µL heptane was added to the vials L100125-9-3 and L100125-9-4 with no movement in the system.

Additional experiments were also performed with IPA:Water solvent systems. The details of these experiments are provided in Table 29.

TABLE 29

Details of salt formation followed by cooling crystallization experiments performed with IPA:Water

| Exp ID | Amt of di-Acetate (mg) | Amt of p-TSA monohydrate (mg) | IPA:Water (96.5:3.5 Vol) | Anti-solvent | Amount (µL) | Comment |
|---|---|---|---|---|---|---|
| 125-9-5 | 96.6 | 81.8 | 11 | IPA | 520 | Clear solution, seeded cooled down to 46° C., unstirrable slurry, 400 µL Heptane added and system became flowable |
| 125-9-6 | 84.1 | 70 | 11 | Heptane | 155.2 | Cloudy system, seeded, 310.4 µL Heptane added, system gummed and gum persisted | over a span of 7 minutes and the system was left stirring. Improvement in flowability was observed upon Heptane addition.

The system was kept for 40 minutes and 2 additional volumes of Heptane was added. The system was cooled to RT naturally and 2 additional volumes of Heptane were added. A better flowable slurry was observed in the case of 125-7-2 (in 4 mL vial), while a thick yet stirrable slurry was observed in the case of experiment 125-7-1 (in 2 mL vial).

This led to a hypothesis that the flowability and rheology of the system is dependent on shear forces with better stirring producing better flowability.

Salt Formation and Cooling Crystallization Experiments with IPA:MeOH and IPA:Water Solvent Systems Salt formation starting with di-acetate of SBT-020 and p-toluene sulfonic acid monohydrate followed by cooling crystallization experiments were performed in IPA:MeOH Both vials were cooled to 52° C. and held for 10 minutes with no precipitation. Anti-solvent addition followed by seeding was performed at this temperature. All the vials were cooled down to RT and were kept at RT for 10 days. XRPD was performed on all the vials after 10 days. No observable change in the rheology was observed in all cases. All the XRPD patterns revealed the solid to be the same form that was consistently observed, however the solid produced by the addition of Heptane as the anti-solvent (L100125-10-6) showed relatively lower intensity for the peak at '2θ' of about 4° C.

Scale-Up Salt Formation Followed by Cooling Crystallization in EasyMax 402

Due to the success in the solvent systems IPA:Water, a scale-up was performed in a 100 mL EasyMax 402 starting with ~2.5 g of di-Acetate. A detailed description of the procedure followed is given below:

2.196 g of di-Acetate of SBT-020 was added to a 100 mL EasyMax reactor flask. 11 Vol IPA:Water (96.5:3.5 Vol) was added to this di-Acetate and complete dissolution was observed at RT.

1.8361 g of p-Toluene sulfonic acid monohydrate (~3.15 Eq) were added to this solution and dissolution was observed. The Jacket temperature of the reactor was adjusted to 65° C., the system was stirred for few minutes.

The reactor temperature (Bulk system) was adjusted to 50° C. and after the system reached this temperature a small spec of seed from the experiment L100125-7-2 (Cooling crystallization of Tosylate of SBT-020 in IPA:Water system in a 4 mL vial). System became cloudy in about 10 minutes.

The system is cooled to 40° C. over 5 hours.

4 Volumes of IPA was added for 30 minutes when the reactor temperature was 42° C. during the cooling ramp. System was very thick slurry before the addition of IPA.

The system was kept at 40° C. for 2 hours and was cooled to 25° C. over 7 hours. The system was kept at 25° C. for 1 hour and was observed to be very viscous.

4 V Heptane was added and the viscosity of the system did not change. The system had a yogurt like consistency. The whole system was filtered and washed with 6 V IPA. Filtration time was about 5 minutes to filter ~45-50 mL of the system.

The solid was dried in vacuum oven at RT. XRPD was performed on sample before Heptane addition and also after filtration. The morphology of the sample before Heptane addition was needle like.

3 g of Tri-tosylate of SBT-020 was obtained after drying. However, drying the solid resulted in a solid that is almost amorphous with very faint signs of crystallinity.

Additional Experiments Performed to Remove IPA

Two additional experiments were performed to remove IPA from the Tosylate of SBT-020 obtained in the EasyMax experiment.

1. The dry Tosylate of SBT-020 was added to a 4 mL vial and was dried in a vacuum oven at 50° C. for about 6 hours under active vacuum and under passive vacuum overnight. (L100125-14-1).

2. 242 mg of the dry Tosylate of SBT-020 from the EasyMax experiment was slurried in 10 V of MeOAc at 50° C. for 2 hours, filtered and washed with 4 V MeOAc. This solid was dried in a vacuum oven at 50° C. for 6 hours under active vacuum and under passive vacuum overnight. (L100125-14-1).

Both solids were subjected to H-NMR and did not show the presence of any residual solvent. However, an extra peak was observed at a peak shift of 2.6 ppm in D2O.

Attempts to Make Crystalline Salts of SBT-020 with the Counter-Ions p-Bromo Benzoic Acid and p-Bromo Benzene Sulfonic Acid Experiments with p-Bromo Benzoic Acid Experiments were performed in an attempt to make salts of SBT-020 with Bromo benzoic Acid starting. The procedure followed is provided below:

About ~100 mg of the Di-Acetate of SBT-020 were mixed with 3 equiv. of p-Bromo benzoic Acid.

7 V of the respective solvent is added and the vials are heated to 50° C.

The vials are kept at this temperature for 45 minutes and were cooled down to RT and were stirred O/N.

The details of these experiments are shown in Table 30.

TABLE 30

Experiments performed in an attempt to make Bromo Benzoate of SBT-020

| Exp ID | Amt of di-Acetate (mg) | Amt of CI (mg) | Solvent | Observation |
| --- | --- | --- | --- | --- |
| 122-88-3 | 103.1 | 89.4 | EtOH | Thin slurry at 50° C., slurry at RT |
| 122-88-4 | 102.7 | 89.1 | IPA | Thin slurry at 50° C., thick slurry at RT |
| 122-88-5 | 101.3 | 90.5 | MIBK | Gum |
| 122-88-6 | 98.3 | 88.9 | EtOH:MeOAc (1:1) | very thin slurry at RT |
| 122-88-7 | 98 | 88.6 | BA | Thin slurry at 50° C., slurry at RT |

A small amount of the slurry from vials L100122-88-3, 88-4 and 88-7 was filtered and was subjected to XRPD.

The XRPD pattern of the solid produced in IPA (L100122-88-4) showed some features that are different from the CI. So this slurry is filtered, dried at RT in vacuum oven and was subjected to HPLC analyses. However, no presence of SBT-020 was identified.

Experiments with the Counter-Ion p-Bromo Benzene Sulfonic Acid

Experiments were performed to make salts of SBT-020 with p-Bromo Benzene Sulfonic Acid. The same procedure followed for p-Bromo Benzoic Acid was implemented. The details of these experiments are shown in Table 31.

TABLE 31

Details of experiments being performed to produce p-Bromo Benzene Sulfonate salts of SBT-020

| Exp ID | Amt of di-Acetate | Amt of CI | Solvent | Observation |
| --- | --- | --- | --- | --- |
| 122-90-3 | 27.1 | 29 | BA | Dissolved at RT |
| 122-90-4 | 25.1 | 32.3 | EtOH | Dissolved at RT |
| 122-90-5 | 24.2 | 28.1 | IPA | Oil:Gum |
| 122-90-6 | 26.1 | 30.4 | MIBK | Gum |
| 122-90-7 | 27.2 | 31.6 | EtOH:MeOAc (1:1) | Dissolved at RT |

The vials 122-90-3, 90-4 and 90-7 are being evaporated to recover the solids and will be subjected to characterization. The vials from the experiment L100122-90-4 and 122-90-7 were re-slurried in 5V MIBK and MEK respectively. The experiment in MIBK resulted in a good slurry while the experiment in MEK resulted in gumming XRPD was performed on the solid from the slurry as well as the gum. The gum from the experiment in MEK showed signs of crystallinity.

Example 2. Salt of SBT-020 with L-Lysine as CI-XRPD Peak List

TABLE 32

| Peak No. | 2-theta(°) | d-spacing(Å) | Height(counts) | Rel. Height (% of strongest reflection) |
| --- | --- | --- | --- | --- |
| 1 | 4.2261 | 20.89149 | 4689.32 | 100.0 |
| 2 | 5.0243 | 17.57411 | 5.59 | 0.1 |
| 3 | 6.6588 | 13.26344 | 78.93 | 1.7 |

TABLE 32-continued

| Peak No. | 2-theta(°) | d-spacing(Å) | Height(counts) | Rel. Height (% of strongest reflection) |
|---|---|---|---|---|
| 4 | 8.2982 | 10.64651 | 1720.94 | 36.7 |
| 5 | 8.6421 | 10.22361 | 30.87 | 0.7 |
| 6 | 10.0369 | 8.80577 | 83.82 | 1.8 |
| 7 | 10.9707 | 8.05821 | 116.14 | 2.5 |
| 8 | 12.3486 | 7.16197 | 643.4 | 13.7 |
| 9 | 16.4828 | 5.37375 | 1337.77 | 28.5 |
| 10 | 19.6073 | 4.5239 | 168.02 | 3.6 |
| 11 | 20.1651 | 4.40001 | 2.45 | 0.1 |
| 12 | 24.8069 | 3.58621 | 1513.14 | 32.3 |
| 13 | 29.0247 | 3.07394 | 446.97 | 9.5 |

Example 3. Salt of SBT-020 with L-Lysine as CI-XRPD Peak List—Pattern 2

TABLE 33

| Peak No. | 2-theta(°) | d-spacing(Å) | Height(counts) | Rel. Height (% of strongest reflection) |
|---|---|---|---|---|
| 1 | 4.4004 | 20.06438 | 6383.71 | 100.0 |
| 2 | 5.4676 | 16.15033 | 1.24 | 0.0 |
| 3 | 6.7036 | 13.17507 | 358.7 | 5.6 |
| 4 | 8.4749 | 10.42488 | 1237.48 | 19.4 |
| 5 | 8.9195 | 9.90623 | 1289.3 | 20.2 |
| 6 | 11.1651 | 7.91836 | 460.65 | 7.2 |
| 7 | 12.2024 | 7.24749 | 305.83 | 4.8 |
| 8 | 15.6936 | 5.64217 | 617.47 | 9.7 |
| 9 | 16.4475 | 5.38522 | 439.47 | 6.9 |
| 10 | 17.7995 | 4.9791 | 15.22 | 0.2 |
| 11 | 18.5661 | 4.77519 | 128.92 | 2.0 |
| 12 | 19.8016 | 4.47996 | 468.6 | 7.3 |
| 13 | 24.7466 | 3.59482 | 996.19 | 15.6 |
| 14 | 25.663 | 3.46848 | 4.8 | 0.1 |
| 15 | 26.1011 | 3.41125 | 106.26 | 1.7 |
| 16 | 29.1061 | 3.06553 | 197.5 | 3.1 |

Example 4. Salt of SBT-020 with L-Arginine as CI-XRPD Peak List

TABLE 34

| Peak No. | 2-theta(°) | d-spacing(Å) | Height(counts) | Rel. Height (% of strongest reflection) |
|---|---|---|---|---|
| 1 | 7.2369 | 12.20532 | 1113.27 | 100 |
| 2 | 10.2443 | 8.62796 | 1052.95 | 94.58173 |
| 3 | 18.5712 | 4.77391 | 810.53 | 72.80624 |
| 4 | 19.9056 | 4.45678 | 812.23 | 72.95894 |
| 5 | 20.5017 | 4.32852 | 1206.89 | 108.4095 |
| 6 | 22.3429 | 3.97582 | 1309.04 | 117.5851 |
| 7 | 25.8406 | 3.44505 | 220.06 | 19.76699 |
| 8 | 26.8697 | 3.31539 | 632.98 | 56.85773 |
| 9 | 27.6899 | 3.21903 | 10.36 | 0.930592 |
| 10 | 29.5416 | 3.02133 | 171.12 | 15.46076 |

Example 5. Salt of SBT-020 with L-Seine as CI-XRPD Peak List

TABLE 35

| Peak No. | 2-theta(°) | d-spacing(Å) | Height(counts) |
|---|---|---|---|
| 1 | 16.3125 | 5.42946 | 2400.54 |
| 2 | 17.2726 | 5.12976 | 110.89 |
| 3 | 18.4711 | 4.79955 | 30.81 |
| 4 | 19.0356 | 4.65846 | 650.73 |
| 5 | 20.6684 | 4.29399 | 177.57 |
| 6 | 21.1735 | 4.19268 | 8.81 |
| 7 | 21.6748 | 4.09684 | 11.01 |
| 8 | 22.0235 | 4.03275 | 3.51 |
| 9 | 22.8225 | 3.89334 | 2102.71 |
| 10 | 23.4813 | 3.78558 | 75.17 |
| 11 | 24.8323 | 3.58259 | 108.53 |
| 12 | 26.1425 | 3.40594 | 74.64 |
| 13 | 26.9707 | 3.30321 | 49.64 |
| 14 | 28.2387 | 3.15769 | 772.12 |

Example 6. Salt of SBT-020 with Tosylate as CI-XRPD Peak List

TABLE 36

| Peak No. | 2-theta(°) | d-spacing(Å) | Hight(counts) | Rel. Height (% of strongest reflection) |
|---|---|---|---|---|
| 1 | 4.2472 | 20.7876 | 2997.56 | 100 |
| 2 | 5.6124 | 15.73391 | 627.05 | 20.9 |
| 3 | 6.005 | 14.70599 | 4.46 | 0.1 |
| 4 | 6.5059 | 13.57485 | 259.61 | 8.7 |
| 5 | 7.3139 | 12.07693 | 343.69 | 11.5 |
| 6 | 8.3849 | 10.5366 | 597.95 | 19.9 |
| 7 | 9.0331 | 9.78189 | 360.91 | 12.0 |
| 8 | 9.3884 | 9.41252 | 8.45 | 0.3 |
| 9 | 10.976 | 8.05436 | 122.16 | 4.1 |
| 10 | 11.6992 | 7.55801 | 283.45 | 9.5 |
| 11 | 12.2816 | 7.20088 | 49.9 | 1.7 |
| 12 | 12.8483 | 6.88455 | 78.09 | 2.6 |
| 13 | 13.6768 | 6.4693 | 381.28 | 12.7 |
| 14 | 14.5232 | 6.09412 | 263.75 | 8.8 |
| 15 | 15.3546 | 5.76598 | 6.3 | 0.2 |
| 16 | 16.434 | 5.38962 | 400.27 | 13.4 |
| 17 | 16.79 | 5.27613 | 354.73 | 11.8 |
| 18 | 17.4904 | 5.0664 | 81.02 | 2.7 |
| 19 | 17.9183 | 4.94637 | 103.92 | 3.5 |
| 20 | 18.5267 | 4.78527 | 201.51 | 6.7 |
| 21 | 19.2386 | 4.60977 | 655.29 | 21.9 |
| 22 | 19.8404 | 4.47128 | 976.61 | 32.6 |
| 23 | 20.5197 | 4.32477 | 13.29 | 0.4 |
| 24 | 20.8647 | 4.25402 | 218.71 | 7.3 |
| 25 | 21.3043 | 4.16724 | 12.68 | 0.4 |
| 26 | 21.7736 | 4.07847 | 667.45 | 22.3 |
| 27 | 22.1003 | 4.0189 | 300.84 | 10.0 |
| 28 | 22.656 | 3.92158 | 317.72 | 10.6 |
| 29 | 23.2875 | 3.81664 | 7.74 | 0.3 |
| 30 | 23.7016 | 3.75089 | 6.32 | 0.2 |
| 31 | 24.3712 | 3.64933 | 578.49 | 19.3 |
| 32 | 24.9261 | 3.56933 | 614.26 | 20.5 |
| 33 | 25.4669 | 3.49475 | 4.17 | 0.1 |
| 34 | 25.7584 | 3.45585 | 183.06 | 6.1 |
| 35 | 26.8617 | 3.31636 | 51.28 | 1.7 |
| 36 | 27.8642 | 3.19928 | 31.47 | 1.0 |
| 37 | 29.0847 | 3.08775 | 215.72 | 7.2 |

What is claimed is:

1. A crystalline form of a salt of Compound (I),

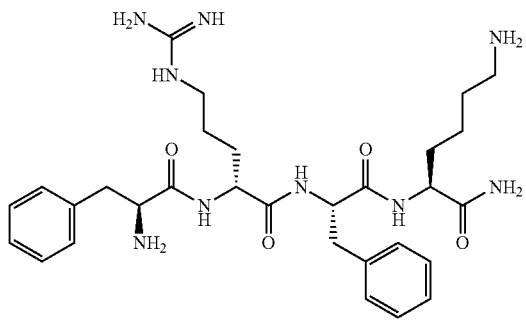
(I)

wherein said crystalline form has characteristic peaks in its x-ray powder diffraction (XRPD) pattern at values of two theta as described in any one of Tables 32-36;

wherein the values of two theta described in Table 32 are:

| |
|---|
| 4.2261 |
| 5.0243 |
| 6.6588 |
| 8.2982 |
| 8.6421 |
| 10.0369 |
| 10.9707 |
| 12.3486 |
| 16.4828 |
| 19.6073 |
| 20.1651 |
| 24.8069 |
| 29.0247 | wherein the values of two theta described in Table 33 are:

| |
|---|
| 4.4004 |
| 5.4676 |
| 6.7036 |
| 8.4749 |
| 8.9195 |
| 11.1651 |
| 12.2024 |
| 15.6936 |
| 16.4475 |
| 17.7995 |
| 18.5661 |
| 19.8016 |
| 24.7466 |
| 25.663 |
| 26.1011 |
| 29.1061 | wherein the values of two thea described in Table 34 are:

| |
|---|
| 7.2369 |
| 10.2443 |
| 18.5712 |
| 19.9056 |
| 20.5017 |
| 22.3429 |
| 25.8406 |
| 26.8697 |
| 27.6899 |
| 29.5416 | wherein the values of two theta described in Table 35 are:

| |
|---|
| 16.3125 |
| 17.2726 |
| 18.4711 |
| 19.0356 |
| 20.6684 |
| 21.1735 |
| 21.6748 |
| 22.0235 |
| 22.8225 |
| 23.4813 |
| 24.8323 |
| 26.1425 |
| 26.9707 |
| 28.2387 | wherein the values of two theta described in Table 36 are:

| |
|---|
| 4.2472 |
| 5.6124 |
| 6.005 |
| 6.5059 |
| 7.3139 |
| 8.3849 |
| 9.0331 |
| 9.3884 |
| 10.976 |
| 11.6992 |
| 12.2816 |
| 12.8483 |
| 13.6768 |
| 14.5232 |
| 15.3546 |
| 16.434 |
| 16.79 |
| 17.4904 |
| 17.9183 |
| 18.5267 |
| 19.2386 |
| 19.8404 |
| 20.5197 |
| 20.8647 |
| 21.3043 |
| 21.7736 |
| 22.1003 |
| 22.656 |
| 23.2875 |
| 23.7016 |
| 24.3712 |
| 24.9261 |
| 25.4669 |
| 25.7584 |
| 26.8617 |
| 27.8642 |
| 29.0847. |

2. A crystalline form of a salt of Compound (I),

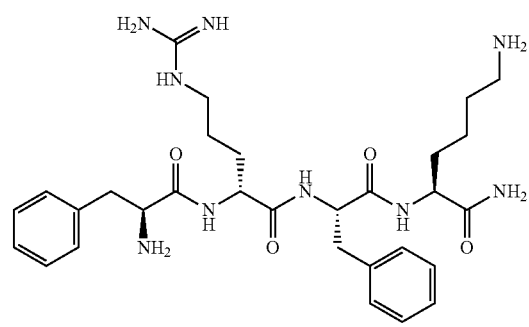
(I)

wherein said crystalline form has characteristic peaks in its x-ray powder diffraction (XRPD) pattern as described in any one of FIGS. 1-5.

3. A crystalline form of a lysine salt of Compound (I),

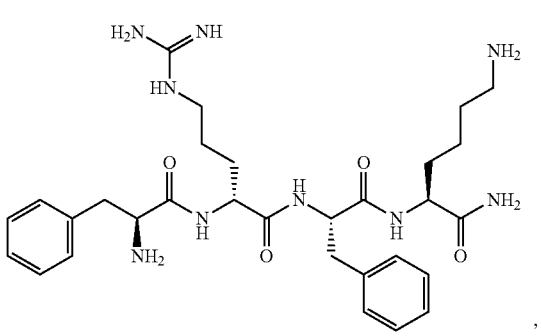
(I)

wherein said crystalline form has characteristic peaks in its x-ray powder diffraction (XRPD) pattern at values of two theta (° 2θ) of: 4.2, 8.3, 12.3, 16.5, 24.8, and 29.0.

4. The crystalline form of claim 3, wherein said crystalline form has characteristic peaks in its XRPD pattern at values of two theta (° 2θ) of: 4.2, 5.0, 6.6, 8.3, 8.6, 10.0, 11.0, 12.3, 16.5, 19.6, 20.2, 24.8, and 29.0.

5. A crystalline form of a lysine salt of Compound (I),

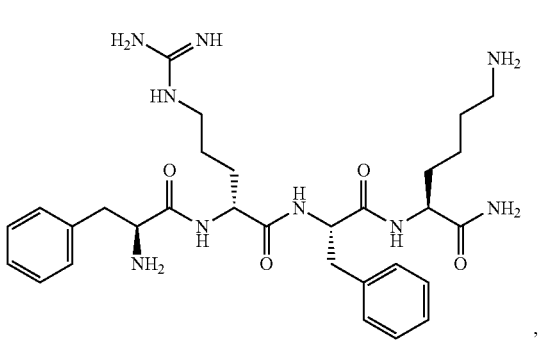
(I)

wherein said crystalline form has characteristic peaks in its x-ray powder diffraction (XRPD) pattern at values of two theta (° 2θ) of: 4.4, 6.7, 8.5, 8.9, 11.2, 15.7, 16.4, 19.8, and 24.7.

6. The crystalline form of claim 5, wherein said crystalline form has characteristic peaks in its XRPD pattern at values of two theta (° 2θ) of: 4.4, 5.5, 6.7, 8.5, 8.9, 11.2, 12.2, 15.7, 16.4, 17.8, 18.6, 19.8, 24.7, 25.7, 26.1, and 29.1.

7. A crystalline form of an arginine salt of Compound (I),

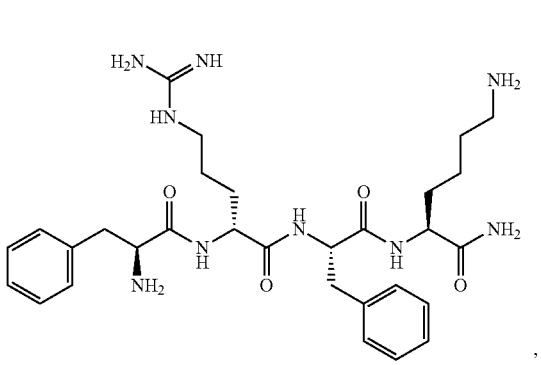
(I)

wherein said crystalline form has characteristic peaks in its x-ray powder diffraction (XRPD) pattern at values of two theta (° 2θ) of: 7.2, 10.2, 18.6, 19.9, 20.5, 22.3, and 26.9.

8. The crystalline form of claim 7, wherein said crystalline form has characteristic peaks in its XRPD pattern at values of two theta (° 2θ) of: 7.2, 10.2, 18.6, 19.9, 20.5, 22.3, 25.8, 26.9, 27.7, and 29.5.

9. A crystalline form of a serine salt of Compound (I),

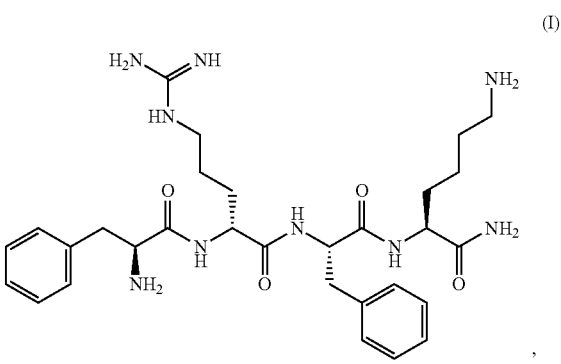 [SMILES: N=C(N)NCCC[C@@H](NC(=O)[C@@H](N)Cc1ccccc1)C(=O)N[C@@H](Cc1ccccc1)C(=O)N[C@@H](CCCCN)C(N)=O]
(I)

wherein said crystalline form has characteristic peaks in its x-ray powder diffraction (XRPD) pattern at values of two theta (° 2θ) of: 16.3, 17.3, 19.0, 20.7, 22.8, 23.5, 24.8, and 28.2.

10. The crystalline form of claim 9, wherein said crystalline form has characteristic peaks in its XRPD pattern at values of two theta (° 2θ) of: 16.3, 17.3, 18.5, 19.0, 20.7, 21.2, 21.7, 22.0, 22.8, 23.5, 24.8, 26.1, 27.0, and 28.2.

11. A crystalline form of a tosylate salt of Compound (I),

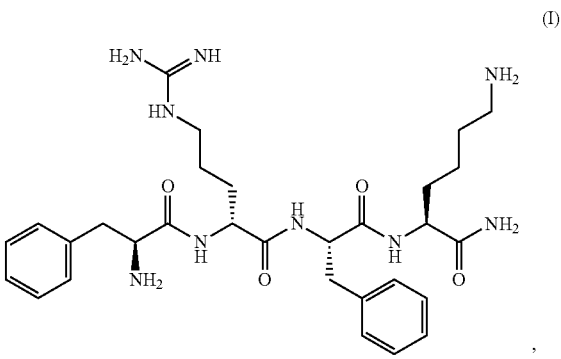 [SMILES: N=C(N)NCCC[C@@H](NC(=O)[C@@H](N)Cc1ccccc1)C(=O)N[C@@H](Cc1ccccc1)C(=O)N[C@@H](CCCCN)C(N)=O]
(I)

wherein said crystalline form has characteristic peaks in its x-ray powder diffraction (XRPD) pattern at values of two theta (° 2θ) of: 4.2, 5.6, 8.4, 19.2, 19.8, 21.8, 24.4, and 24.9.

12. The crystalline form of claim 11, wherein said crystalline form has characteristic peaks in its XRPD pattern at values of two theta (° 2θ) of: 4.2, 5.6, 7.3, 8.4, 9.0, 13.7, 16.4, 16.8, 19.2, 19.8, 21.8, 22.1, 22.7, 24.4, and 24.9.

13. A composition, comprising a crystalline form of claim 1.

14. A process for making a pharmaceutical composition comprising Compound (I),

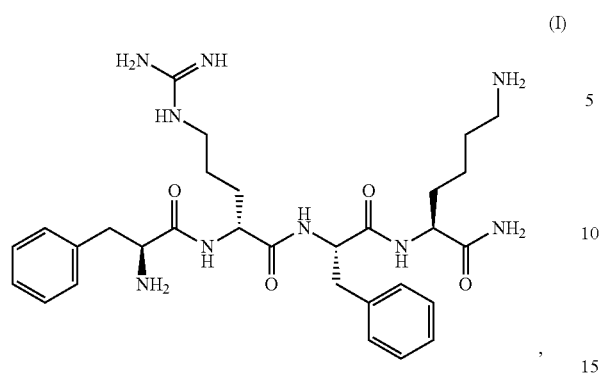
comprising dissolving a crystalline form of claim 1.
\* \* \* \* \*